(12) United States Patent
Happe

(10) Patent No.: US 7,244,618 B2
(45) Date of Patent: Jul. 17, 2007

(54) STABLE LIPID STANDARDS

(75) Inventor: Thomas Happe, Windham, ME (US)

(73) Assignee: Maine Standards Company, LLC, Windham, ME (US)

( * ) Notice: Subject to any disclaimer, the term of this patent is extended or adjusted under 35 U.S.C. 154(b) by 0 days.

(21) Appl. No.: 11/216,809

(22) Filed: Aug. 31, 2005

(65) Prior Publication Data

US 2006/0046301 A1    Mar. 2, 2006

Related U.S. Application Data

(60) Provisional application No. 60/606,224, filed on Sep. 1, 2004.

(51) Int. Cl.
*G01N 33/92* (2006.01)
*G01N 31/00* (2006.01)

(52) U.S. Cl. .............. 436/71; 436/8; 436/13; 422/61; 252/408.1

(58) Field of Classification Search ............ 436/8, 436/13, 18, 71; 422/61; 252/408.1
See application file for complete search history.

(56) References Cited

U.S. PATENT DOCUMENTS

| 4,239,649 | A | | 12/1980 | Gindler et al. | |
| 4,289,649 | A | * | 9/1981 | Harders et al. | 436/13 |
| 4,363,633 | A | | 12/1982 | Christiansen | |
| 4,476,224 | A | | 10/1984 | Adler | |
| 4,643,976 | A | | 2/1987 | Hoskins | |
| 4,701,417 | A | | 10/1987 | Portenhauser et al. | |
| 4,716,119 | A | | 12/1987 | Rehner et al. | |
| 4,868,139 | A | | 9/1989 | Deeg et al. | |
| 4,996,073 | A | | 2/1991 | Copeland et al. | |
| 5,240,851 | A | | 8/1993 | Paridans et al. | |
| 5,258,308 | A | * | 11/1993 | Freeman et al. | 436/8 |
| 5,270,208 | A | * | 12/1993 | Ryan | 436/10 |
| 5,401,639 | A | * | 3/1995 | Saldivar, Jr. et al. | 435/14 |
| 5,547,873 | A | * | 8/1996 | Magneson et al. | 436/18 |
| 5,770,451 | A | * | 6/1998 | Ryan et al. | 436/13 |
| 5,817,519 | A | * | 10/1998 | Zelmanovic et al. | 436/63 |
| 5,854,073 | A | * | 12/1998 | Burns et al. | 436/12 |
| 5,891,734 | A | | 4/1999 | Gill et al. | |
| 6,372,503 | B1 | | 4/2002 | Samsoondar | |

FOREIGN PATENT DOCUMENTS

EP    0684477 A2    11/1995

* cited by examiner

*Primary Examiner*—Maureen M. Wallenhorst
(74) *Attorney, Agent, or Firm*—Drinker Biddle + Reath, LLP

(57) ABSTRACT

The invention describes materials useful for calibrating methods, and standards, calibration verification, linearity, and quality control materials for any method used to detect lipids and/or lipoproteins. This invention describes methods for producing, and compositions produced thereby, stable lipid controls, standards, and reagents including a stabilizing amount of TDPA, and further including a known amount of a substantially pure constituent of interest, including total cholesterol (CHOL), triglycerides (TRIG), high density lipoprotein (HDL), APO lipoprotein A (APO-A), APO Lipoprotein B (APO-B), low density lipoprotein (LDL), apolipoprotein a Lp(a) and other lipoprotein moieties useful for calibrating, standardizing, verifying, quality control, and the like, relating to use of an instrument for assessing the level of such constituents in a sample.

38 Claims, No Drawings

STABLE LIPID STANDARDS

CROSS-REFERENCE TO RELATED APPLICATIONS

The present application is entitled to priority under 35 U.S.C. § 119(e), to U.S. Provisional Application No. 60/606,224, filed on Sep. 1, 2004, which application is hereby incorporated herein by reference in its entirety.

BACKGROUND OF THE INVENTION

Determination of lipid levels in a body fluid, particularly determination of total cholesterol, high density lipoprotein (HDL), low density lipoprotein (LDL), triglycerides, apolipoprotein, phospholipids, sphingolipids and cholesteryl esters levels, collectively referred to as "lipids", has rapidly come into wide use with the recent development of enzymatic, immunologic, electrophoretic and ultracentrifugation determination processes. As a result, the utility of these lipids in the field of clinical diagnosis has been increasing. Therefore, a proper standard solution for determination of lipid levels is required.

Most cholesterol analyses comprise mixing a chromogenic working reagent with the sample to be analyzed and, after color development, observing color intensity on a spectrophotometer. The working reagent generally contains cholesterol esterase in order to convert cholesterol esters to free cholesterol, and cholesterol oxidase to oxidize free cholesterol yielding cholestenone, simultaneously liberating hydrogen peroxide. The amount of cholesterol present is then determined by measuring the amount of hydrogen peroxide liberated using the peroxidase/phenol/4-aminoantipyrine system, also present in the working reagent. This analysis is also run on calibrator solutions, which are prepared by adding the working reagent to standard solutions containing known concentrations of cholesterol, so that meaningful quantitative information can be obtained.

Most HDL Cholesterol analyses are performed by homogeneous assays without the need for pretreatment of centrifugation steps. The method depends on a unique detergent which solubilizes only the HDL lipoprotein particles and releases HDL cholesterol to react with the enzymatic assay described above to produce a color product. The same detergent also inhibits the reaction of the cholesterol enzymes with LDL, very-low-density lipoproteins (VLDL) and chylomicrons lipoproteins by adsorbing to their surfaces. Furthermore, a polyanion contained in the reagent enhances the selectivity for HDL cholesterol by complexing the LDL, VLDL and chylomicron proteins (see Beckman Synchron CX Systems Chemistry Information Manual No. 249595, May 2000).

HDL Cholesterol analyses are also measured via a direct method using polyethylene glycol (PEG)-modified enzymes and dextran sulfate. When cholesterol esterase and cholesterol oxidase enzymes are modified by PEG, they demonstrate selective catalytic activities toward lipoprotein fractions, with the reactivity increasing in the order: LDL<VLDL<chylomicrons<HDL. In the presence of magnesium ions, sulfated α-cyclodextrin reduces the reactivity of cholesterol, especially in chylomicrons and VLDL, without the need for precipitation of lipoprotein aggregates. (See Roche Diagnostics Corporation, GmbH, 2002, No. 05453101, Mannheim, Germany.) This allows for the selective determination of HDL cholesterol in serum.

To date, LDL Cholesterol assays have been performed taking advantage of the selected micellar solubilization of LDL-cholesterol by a nonionic detergent and the interaction of a sugar compound with lipoproteins (VLDL and chylomicrons). When a detergent is included in the enzymatic method for cholesterol determination, the relative reactivities of cholesterol in the lipoprotein fractions increases in this order: HDL<chylomicrons<VLDL<LDL. In the presence of magnesium cations, a sugar compound markedly reduces the enzymatic reaction for the cholesterol measurement in VLDL and chylomicrons. The combination of a sugar compound with detergent enables the selective determination of LDL cholesterol in serum. (See Roche Diagnostics Corporation, GmbH, 2002, Technical Publication No. 054565801, Mannheim, Germany). LDL cholesterol is also determined using procedures described in technical bulletins available from, among others, Genzyme Corporation, Beckman Coulter, and the like.

Most triglycerides assays comprise mixing a chromogenic working reagent with the sample to be analyzed and, after color development, observing color intensity on a spectrophotometer. The working reagent generally contains lipase to convert triglycerides to glycerol and fatty acids, followed by the reaction of glycerol and ATP catalyzed by glycerol kinase to produce glycerol-3-phosphate and ADP. The glycerol-3-phosphate is then catalyzed with glycerophosphate oxidase to form dihydroxyacetone phosphate plus hydrogen peroxide. The amount of triglycerides present is then determined by measuring the amount of color from the reaction of peroxidase converting chromogenic substances such as 4-aminophenazone and 4-chlorophenol or 4-aminoantipyrine and 3,5-dichloro-2-hydroxybenzenesulfonic acid to form the end product for photometric measurement. This analysis is also run on calibrator solutions, which are prepared by adding the working reagent to standard solutions containing known concentrations of triglycerides, so that meaningful quantitative information can be obtained.

Apolipoprotein A-1 (APO-A1) is measured using immuno-turbidimetric assay techniques wherein sample is added to a Tris buffer followed by addition of an anti-lipoprotein A-1 antibody. Anti-lipoprotein A-1 antibodies react with the antigen in the sample to form antigen/antibody complexes which, following agglutination, are measured turbidimetrically. (See Roche Diagnostics Corporation, GmbH, 2002, Technical Publication No. 03032612, Mannheim, Germany).

Apolipoprotein B (APO B) is often measured using immuno-turbidimetric assay techniques wherein sample is added to a Tris buffer followed by addition of an anti-lipoprotein B antibody. Anti-lipoprotein B antibodies react with the antigen in the sample to form antigen/antibody complexes which, following agglutination, are measured turbidimetrically. (See Roche Diagnostics Corporation, GmbH, 2002, Technical Publication No. 03032639, Mannheim, Germany).

These procedures, whether enzymatic, immunologic or turbidimetric, all require that the working reagent, calibrators, quality control (QC) materials and samples be of an aqueous matrix, such as, but not limited to, serum, plasma, and the like. The need for this specific matrix presents a problem with respect to the preparation of calibrator solutions, since cholesterol, and most other components commonly referred to as "lipids", are substantially insoluble in water. For example, a cholesterol standard solution made in alcohol, which when combined with the aqueous working reagents, can produce precipitation of cholesterol. This yields an unacceptable calibrator solution. Such precipitation can lead to uncertain or incompatible color development in the calibrator, QC or calibration verification and/or linearity materials and generally makes the selected specimen useless for reliably correlating color intensity with cholesterol concentration. In a second example, measurement of triglycerides with a reference method uses a triglycerides standard made up of triolein and/or tripalmitin in an alcohol matrix.

Due to their hydrophobicity, lipids are generally dissolved in an organic solvent. These solutions can then be used in the Abell-Kendall reference method for cholesterol determination. In this technique, the solvent solubilized cholesterol is compatible with the assay methodology. However, the lipids in these standard solutions differ in their existing state and fluid property from those found in serum. Thereby, the reactivity between the standard solution and the body fluid (e.g., serum) differ, resulting in errors in the determined values.

Therefore, human- or animal-derived serum or purified lipoprotein cholesterol has been used as the standard solution. Triglycerides may alternately be calibrated using materials such as an artificial water-soluble glycerol, water insoluble animal egg yolk extracts, endogenous triglycerides or water-insoluble solvent-based (alcohol) triolein/tripalmitin standards. For triglyceride calibration, the use of glycerol is not preferred in cases where free glycerol may be present in the sample thus necessitating a "glycerol blanking" prior to lipase conversion of the triglycerides to glycerol in the reaction scheme. The National Institute for Standards and Technology (NIST) has Standard Reference Materials (SRM) available for Total Cholesterol, Total Glycerides, Triglycerides, HDL-Cholesterol and LDL-Cholesterol. These SRMs (SRM 1951a and 1951b) consist of reference concentration values that are lot-specific. The matrixes for these SRMs consists of "Lipids in Frozen Human Serum", shipped under dry ice and are stable for only one (1) week at −20° C. and at −80° C. for longer periods of time. These media all present high costs, difficult shipping conditions, requirements for a −80° C. storage freezer upon receipt, can contain unknown impurities that can influence the determined values, and present technical difficulties relating the potential presence of infectious agents. Additionally, processes for purifying lipoproteins are technically complex and costly to perform for routine analyses of vast numbers of samples.

Consequently, lipids and/or lipoproteins and other constituents of interest, have been solubilized in water containing a surfactant and used as the standard/reference solution. However, a large amount of surfactant is required for the solubilization of lipids in water. This, in turn, increases the viscosity of the solution making its handling sometimes difficult. Moreover, samples comprising of solubilized lipids, and/or lipoproteins are unstable and demonstrate short shelf life upon storage. To combat this issue, solubilized lipid solutions have been lyophilized. However, post reconstitution of these samples, there is subsequent loss of constituent activity.

Despite the difficulties in preparing known standards for use in various assays, in order to convert a detectable assay signal to a quantitative result (e.g., concentration of the constituent), the assay must first be calibrated. Calibration is performed by running the assay first with a series of samples of predetermined concentrations following instructions from the manufacturer of the assay method used. These samples are referred to as "calibrators." The results obtained by reading the signals from the calibrators are used to generate, by using various curve fit models, a calibration curve spanning the entire assay range. The calibration curve can then be used to determine the concentration of an unknown sample of QC, calibration verification/linearity, or unknown sample from the signal it produces. Since the calibrator often responds differently than patient serum or other test sample, changes in the calibrator with time may render it ineffective or cause erroneous or inaccurate test results. In the art, there is a need for more stable aqueous calibrators and calibration curves, as well as for quality control and calibration verification/linearity materials to assess the continued accuracy of an assay. The present invention meets these needs.

BRIEF SUMMARY OF THE INVENTION

The invention includes a stable aqueous lipid reference standard composition comprising a substantially pure constituent of known value and a stabilizing amount of an antioxidant, the composition ranging in pH from about 6.5 to 8.0.

In one aspect, the reference composition is useful for at least one use selected from the group consisting of calibration, quality control, calibration verification, and assessment of linearity, and further wherein the composition is useful in a pH range from about 6.5 to 9.0.

In another aspect, the use comprises a manual, semi-automated, and fully-automated method comprising an instrument for measurement of the constituent.

In yet another aspect, the antioxidant is 3,3'-thiodipropionic acid (TDPA).

In a further aspect, the stabilizing amount ranges from about 1.1 grams per liter to 18.0 grams per liter.

In another aspect, the constituent is a substantially pure component of at least one constituent selected from the group consisting of total cholesterol (CHOL), triglycerides (TRIG), low density lipoprotein (LDL), high density lipoprotein (HDL), apolipoprotein A (APO-A), apolipoprotein B (APO-B), apolipoprotein a (Lp(a)) and a subcomponent of an apolipoprotein.

In yet another aspect, the subcomponent is at least one subcomponent selected from the group consisting of AII, AIV, B-48, B-100, CI, CII, CIII, D, E1, E2, E3, E4, E5, E6, F, G, H, and J.

In another aspect, the value of CHOL ranges from about 0 to 5000 mg/dL.

In yet another aspect, the value of triglycerides ranges from about 0 to 4000 mg/dL.

In a further aspect, the value of LDL ranges from about 0 to 5000 mg/dL.

In yet a further aspect, the value of HDL ranges from about 0 to 1000 mg/dL.

In another aspect, the value of APO-A ranges from about 0 to 1000 mg/dL.

In a further aspect, the value of APO-B ranges from about 0 to 1000 mg/dL.

In a further aspect, the value of Lp(a) ranges from about 0 to 1200 mg/dL.

In yet a further aspect, the value of the subcomponent ranges from about 0 to 500 mg/dL.

In another aspect, the composition further comprises a buffer comprising N-2-hydroxyethylpiperazine-N-2-ethane sulphonic acid (HEPES) such that the composition ranges in pH from about 6.5 to 8.0.

In yet a further aspect, the composition further comprises an amount of sodium azide less than about 0.09% (weight/volume).

In another aspect, the composition further comprises PROCLIN (2-methyl-4-isothiazlin-3-one) in an amount ranging from about 10 parts per million (ppm) to 100 ppm.

In yet another aspect, the composition further comprises OXYRASE (cell membrane fragments obtained from *E. coli*) in an amount ranging from about 0.05 U/mL to 0.5 U/mL.

The invention includes a stable control or calibration standard composition comprising a stabilizing amount of 3,3'-thiodipropionic acid, the composition further comprising a predetermined content of substantially pure analyte.

The invention also includes a method for producing a stable aqueous lipid reference standard composition comprising a substantially pure constituent of known value and a stabilizing amount of an antioxidant, the composition ranging in pH from about 6.5 to 8.0. The method comprises mixing a liquid comprising water with a known value of a substantially pure constituent to produce a mixture and further adding a stabilizing amount of 3,3'-thiodipropionic acid to the mixture.

The invention includes a method for producing a stable control or calibration standard composition. The method comprises mixing an aqueous solution with a stabilizing amount of 3,3'-thiodipropionic acid, and further comprises adding a predetermined amount of an essentially pure analyte.

In one aspect, the aqueous solution is selected from the group consisting of water, plasma, serum, a solution comprising bovine serum albumin, a solution comprising human serum albumin, and a solution comprising a Good's Buffer.

In another aspect, the method further comprises adding to the mixture an effective amount of an antimicrobial.

In yet another aspect, the analyte is at least one analyte selected from the group consisting of total cholesterol (CHOL), triglycerides (TRIG), low density lipoprotein (LDL), high density lipoprotein (HDL), apolipoprotein A (APO-A), apolipoprotein B (APO-B), apolipoprotein a (Lp (a)) and a sub component of an apolipoprotein.

The invention includes a method for calibration, quality control, calibration verification, or assessment of linearity of an instrument wherein the instrument is adapted to determine an amount of a constituent in a test solution, the method comprising subjecting the instrument to calibration, quality control, calibration verification, or assessment of linearity with a stable aqueous lipid reference standard composition comprising a substantially pure constituent of known value and a stabilizing amount of an antioxidant, the composition ranging in pH from about 6.5 to 8.0.

The invention also includes a method for calibration, quality control, calibration verification, or assessment of linearity of an instrument adapted to determine the amount of an analyte in a test solution. The method comprises subjecting the instrument to calibration, quality control, calibration verification, or assessment of linearity with a stable aqueous lipid reference standard composition comprising a substantially pure constituent of known value and a stabilizing amount of an antioxidant, the composition ranging in pH from about 6.5 to 8.0, where the antioxidant is TDPA.

The invention includes a kit for calibration, quality control, calibration verification, or calibration of linearity of an instrument adapted to determine the amount of a constituent in a test solution. The kit comprises a composition comprising a known amount of the constituent and a stabilizing amount of 3,3'-thiodipropionic acid. The kit further comprises an applicator and an instructional material for the use of the kit.

In one aspect, the composition comprises about 4.0 g/L TDPA, about 0.9 g/L sodium azide, about 40 ppm PRO-CLIN, and further comprises HEPES buffer at about pH 7.4, wherein the pH of the composition ranges from about pH 7.2 to 7.6.

In another aspect, the kit comprises at least one composition selected from the group consisting of:
a) a composition comprising about 10 mg/dL total cholesterol, about 5 mg/dL HDL, about 0 mg/dL triglycerides, about 5 mg/dL LDL, about 15.6 mg/dL APO-A, and about 3.3 mg/dL APO-B;
b) a composition comprising about 200 mg/dL total cholesterol, about 37.5 mg/dL HDL, about 250 mg/dL triglycerides, about 162.5 mg/dL LDL, about 117.2 mg/dL APO-A, and about 106.9 mg/dL APO-B;
c) a composition comprising about 400 mg/dL total cholesterol, about 115 mg/dL HDL, about 500 mg/dL triglycerides, about 285 mg/dL LDL, about 359.4 mg/dL APO-A, and about 187.5 mg/dL APO-B;
d) a composition comprising about 600 mg/dL total cholesterol, about 177.5 mg/dL HDL, about 750 mg/dL triglycerides, about 422.5 mg/dL LDL, about 554.7 mg/dL APO-A, and about 287.0 mg/dL APO-B; and
e) a composition comprising about 800 mg/dL total cholesterol, about 200 mg/dL HDL, about 1000 mg/dL triglycerides, about 600 mg/dL LDL, about 625 mg/dL APO-A, and about 394.7 mg/dL APO-B.

In yet another aspect, the kit comprises at least one composition selected from the group consisting of:
a) a composition comprising about 0 mg/dL total cholesterol, about 0 mg/dL HDL, about 0 mg/dL triglycerides, about 0 mg/dL LDL, about 0 mg/dL APO-A, and about 0 mg/dL APO-B; and
b) a composition comprising about 200 mg/dL total cholesterol, about 60 mg/dL HDL, about 250 mg/dL triglycerides, about 140 mg/dL LDL, about 188 mg/dL APO-A, and about 92 mg/dL APO-B.

In a further aspect, the kit comprises at least one composition selected from the group consisting of:
a) a composition comprising about 100 mg/dL total cholesterol, about 20 mg/dL HDL, about 90 mg/dL triglycerides, about 80 mg/dL LDL, about 63 mg/dL APO-A, and about 53 mg/dL APO-B;
b) a composition comprising about 250 mg/dL total cholesterol, about 50 mg/dL HDL, about 150 mg/dL triglycerides, about 200 mg/dL LDL, about 156 mg/dL APO-A, and about 132 mg/dL APO-B; and
c) a composition comprising about 500 mg/dL total cholesterol, about 100 mg/dL HDL, about 250 mg/dL triglycerides, about 400 mg/dL LDL, about 313 mg/dL APO-A, and about 263 mg/dL APO-B.

In yet a further aspect, the kit comprises at least one composition selected from the group consisting of:
a) a composition comprising about 100 mg/dL total cholesterol, about 25 mg/dL HDL, about 50 mg/dL triglycerides, about 75 mg/dL LDL, about 78 mg/dL APO-A, and about 49 mg/dL APO-B;
b) a composition comprising about 275 mg/dL total cholesterol, about 48.75 mg/dL HDL, about 287.5 mg/dL triglycerides, about 226.25 mg/dL LDL, about 152.25 mg/dL APO-A, and about 150 mg/dL APO-B;
c) a composition comprising about 450 mg/dL total cholesterol, about 72.5 mg/dL HDL, about 525 mg/dL triglycerides, about 377.5 mg/dL LDL, about 226.5 mg/dL APO-A, and about 251 mg/dL APO-B;
d) a composition comprising about 625 mg/dL total cholesterol, about 96.25 mg/dL HDL, about 762.5 mg/dL triglycerides, about 528.75 mg/dL LDL, about 300.75 mg/dL APO-A, and about 352 mg/dL APO-B; and e) a composition comprising about 800 mg/dL total cholesterol, about 120 mg/dL HDL, about 1000 mg/dL triglycerides, about 680 mg/dL LDL, about 375 mg/dL APO-A, and about 453 mg/dL APO-B.

In another aspect, the kit comprises at least one composition selected from the group consisting of:

a) a composition comprising about 0 mg/dL total cholesterol, about 0 mg/dL HDL, about 0 mg/dL triglycerides, about 0 mg/dL LDL, about 0 mg/dL APO-A, and about 0 mg/dL APO-B; and b) a composition comprising greater than about 240 mg/dL total cholesterol, less than about 35 mg/dL HDL, about 100 mg/dL triglycerides, greater than about 190 mg/dL LDL, greater than about 120 mg/dL APO-A, and less than about 120 mg/dL APO-B.

In yet another aspect, the kit comprises at least one composition selected from the group consisting of:

a) a composition comprising about 0 mg/dL total cholesterol, about 0 mg/dL HDL, about 100 mg/dL triglycerides, about 0 mg/dL LDL, about 0 mg/dL APO-A, and about 0 mg/dL APO-B; and b) a composition comprising greater than about 240 mg/dL total cholesterol, less than about 45 mg/dL HDL, about 100 mg/dL triglycerides, greater than about 190 mg/dL LDL, greater than about 120 mg/dL APO-A, and less than about 120 mg/dL APO-B.

DETAILED DESCRIPTION OF THE INVENTION

The invention relates to the discovery that 3,3'-thiodipropionic acid stabilizes aqueous, serum, plasma, and other matrix lipid standards useful for calibration, quality control, and calibration verification/linearity materials for numerous assays. Thus, the invention relates to novel compositions and methods for producing stable reference standards that can be used for, inter alia, calibration, quality control, among other things, in a wide plethora of art-recognized lipid assays. Also, the invention provides novel calibration, quality control, calibration verification and linearity materials comprising the novel stable lipid standards of the invention.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

By the term "applicator," as the term is used herein, is meant any device including, but not limited to, a hypodermic syringe, a pipette, an automatic sample probe and the like, for administering the compounds and compositions of the invention.

"Instructional material," as that term is used herein, includes a publication, a recording, a diagram, product insert or any other medium of expression which can be used to communicate the usefulness of the composition and/or compound of the invention in the kit for effecting, alleviating or treating the various diseases or disorders recited herein. Optionally, or alternately, the instructional material may describe one or more methods of alleviating the diseases or disorders in a cell or a tissue or a mammal, including as disclosed elsewhere herein.

The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Alternately, the instructional material may be obtained on the Internet in a format suitable for electronic file transmission to the user.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Stabilizing amount," as used herein, refers to an amount of a substance or compound that, when added to an aqueous or serum or plasma reference composition, detectably stabilizes a reference composition when compared with the stability of an identical composition to which the substance or compound is not added. That is, the known value of a constituent present in the composition changes less as a function of time or storage conditions in the composition comprising the substance or compound than the value of the identical constituent present in an otherwise identical composition to which the substance or compound is not added.

A "constituent," as used herein generally interchangeably with "analyte," refers to any substance the presence or amount of which is of interest and to be assessed by any method known in the art. Preferably, a constituent refers to any substance relating to, but not limited to, total cholesterol (CHOL), low density lipoprotein (LDL), high density lipoprotein (HDL), triglycerides, apolipoprotein A (APO-A, encompassing A1 and A2), apolipoprotein B (APO-B), apolipoprotein a (Lp(a)), their respective subcomponents and the like. These, and many other constituents of interest, are discussed in, among other art-recognized treatises, Rifai and Warnick (1994, In: Laboratory Measurements of Lipids, Lipoproteins and Apolipoproteins, Rafai and Warnick, eds., AACC Press, Washington, D.C.), and Rafai, Warnick and Dominiczak (2000, In: Handbook of Lipoprotein Testing, Rafai, Warnick and Dominiczak, eds. AACC Press, Washington, D.C.).

By the term "reference composition," as used herein, is meant any composition used for calibration and/or quality control and/or calibration verification and/or assessment of linearity relating to analysis of the level and/or presence of a constituent of interest in a sample. Such reference composition can be used with any method or device for assessing the presence and/or level of the constituent in a sample.

The term "substantially pure", as used herein with regard to, inter alia, a given constituent, means that the constituent is substantially free from other compounds, biological or otherwise, such as those in cellular material, viral material, plasma, blood, bodily fluid, or culture medium, with which the constituent may have been associated (e.g., in the course of production by biochemical or other techniques or before purification from a natural biological source). For instance, the substantially pure constituent is at least 75% (e.g., at least 80, 85, 95, or 99%) pure by dry weight. Purity can be measured by any appropriate standard method, for example, by column chromatography, HPLC analysis, and the like, as well understood in the art.

DESCRIPTION

The invention relates to the discovery of novel stable lipid aqueous (e.g., serum, plasma, other protein base, and the like) matrix standards useful for calibration, quality control, calibration verification and linearity materials relating to various art-known lipid assays using a wide variety of instruments known in the art, or to be developed in the future. More specifically, the invention relates to the surprising discovery that addition of 3,3'-thiodipropionic acid to an aqueous lipid reference standard stabilizes the standard such that its shelf life is greatly extended. These results further provide novel methods for producing the stable aqueous lipid standard, as well as novel assays using the standard, and kits relating thereto.

I. Composition Comprising a Novel Reference Standard

The invention encompasses a stable aqueous (e.g., serum, plasma, etc.) matrix lipid reference composition. The composition comprises a substantially pure constituent of known value and a stabilizing amount of 3,3'-thiodipropionic acid (TDPA; CAS Registry Number 111-17-1), which is known by various other names, including, but not limited to, 3,3'-thiobispropanoic acid, β,β'-thiodipropionic acid, diethyl sulfide 2,2'-dicarboxylic acid, thiodihydracrylic acid, Tyox A, 4-thiaheptainedioic acid, bis(2-carboxyethyl)sulfide. This is because the data disclosed elsewhere herein demonstrates that an aqueous solution comprising TDPA and at least one constituent being assayed (e.g., total cholesterol, LDL, HDL, APO-A, APO-B, triglycerides, Lp(a) and the like) can be stabilized resulting in greater shelf-life than the identical solution to which TDPA is not added.

Thus, the invention encompasses a stable control or calibration standard composition comprising a stabilizing amount of 3,3'-thiodipropionic acid, and a predetermined content of an analyte, i.e., a specific component, in a test sample, including, but not limited to, a biological sample (that is, a sample obtained from an organism, whether living or deceased).

One skilled in the art, based upon the disclosure provided herein, would readily appreciate that a constituent comprises a wide plethora of substances and compounds of interest that are being assayed for in a test sample. That is, the reference composition can be used to calibrate, to verify the calibration of, and/or as a quality control sample for use with, an instrument that is being used to assess the amount of the constituent of interest. More particularly, as amply demonstrated elsewhere herein, a reference composition comprising TDPA in an amount sufficient to stabilize the composition and a known amount of the constituent, can be used as a standard to calibrate and/or to run quality control on the assay such that the value of the constituent in the test sample can be accurately determined relative to the known value of the same constituent in the reference composition.

The skilled artisan would also appreciate, based upon the disclosure provided herein, that where a test sample is analyzed to detect the presence and/or quantity of a constituent of interest, the results of assaying the test sample are generally compared to a standard to assess the presence and/or amount of the constituent in the test sample. Thus, there exists a need for an accurate reference composition for calibration of the assay, to obtain a reliable calibration curve for any instrument used in the assay, and/or as a quality control and/or calibration verification and linearity to monitor the accuracy of the assay. That is, a reference standard can be used to calibrate an instrument, to periodically verify that the instrument is still operating within the tolerances desired, or both. A discussion of calibration and quality control reference standards is set forth in, for instance, European Patent Application No. 95201336.5 (published as EP 0 684 477A2) of Bahar et al., U.S. Pat. No. 4,239,649 to Gindler et al., U.S. Pat. No. 4,363,633 to Christiansen, U.S. Pat. No. 4,643,976 to Hoskins, U.S. Pat. No. 4,701,417 to Portenhouser et al., U.S. Pat. No. 4,716,119 to Rehner et al., U.S. Pat. No. 4,868,139 to Deeg et al., and U.S. Pat. No. 6,372,503 to Samsoodar, each of which is incorporated by reference herein as if set forth in its entirety.

As demonstrated herein, the stabilizing amount of TDPA is that amount that mediates a detectable increase in the stability, e.g., the shelf life, among other things, of a reference composition when compared with the stability of an identical reference composition to which TDPA is not added. Preferably, the amount ranges from about 1.1 to 18 grams per liter. More preferably, the amount ranges from about 2.6 to about 12.0, even more preferably, from about 3.3 to 10.5, yet more preferably, from about 3.65 to 9.75, even more preferably, from about 4.0 to 9.0, and most preferably, the amount is 4.0 grams per liter (g/L).

As described in detail elsewhere herein, TDPA can function as an antioxidant. In particular, TDPA can function as an antioxidant for the purpose of stabilizing a composition of the present invention. Other antioxidants useful in the present invention include, but are not limited to, monothioglycerol, fumaric acid, ethylenediaminetetraacetic acid (EDTA), butylated hydroxytoluene (BHT), N-acetyl-L-cysteine, OXYRASE, ascorbic acid, phytic acid dodecasodium salt, and the like. The skilled artisan, when armed with the present disclosure, will understand how to identify and characterize an antioxidant useful in the present invention, based on the teachings set forth herein.

It will also be understood that combinations of two or more antioxidants may be used in the present invention. By way of a non-limiting example, OXYRASE and TDPA may be used. It will further be understood, based on the present disclosure, that various concentrations of antioxidants may be used in the present invention. Additionally, it will be understood that various concentrations of antioxidants, and combinations thereof, are encompassed by the present invention, with respect to various standards, including, but not limited to, HDL, LDL, APOA, APOB, CHOL, Lp(a) and TRIG, and that any assay or reaction conditions can be varied, based on the intended use and/or application of a composition or method of the present invention.

It will also be understood, based on the invention set forth herein, that certain antioxidants may not be compatible with other antioxidants, with other combinations of antioxidants, or with certain standard solutions (eg. certain lipids, certain triglycerides, among others). By way of a non-limiting example, and as set forth in Experimental Example 10, certain antioxidants, such as ascorbic acid, may interfere with one or more downstream assays conducted with the standard solution containing the ascorbic acid, such as a peroxidase indicator assay. In another non-limiting example, monothioglycerol, when used as an antioxidant in a TRIG solution, may contribute to a triglyceride hydrolase reaction by falsely increasing glycerol in an indicator reaction.

The invention encompasses a wide range of values of a substantially pure constituent component of the reference composition. That is, as would be understood by the skilled artisan once armed with the teachings provided herein, the invention encompasses a reference composition comprising a plethora of values for any constituent of interest, and any combination thereof. While not limited to any particular constituent or value of a constituent, the invention encompasses numerous constituents such as, but not limited to, total cholesterol (CHOL), low density lipoprotein (LDL), high density lipoprotein (HDL), triglycerides, apolipoprotein A (APO-A, encompassing A1 and A2), apolipoprotein B (APO-B), apolipoprotein a (Lp(a)) their respective subcomponents and the like. These, and many other constituents of interest, are discussed in, among other treatises, Rifai and Warnick (1994, In: Laboratory Measurements of Lipids, Lipoproteins and Apolipoproteins, Rafai and Warnick, eds., AACC Press, Washington, D.C.) and Rafai, Warnick and Dominiczak (2000, In: Handbook of Lipoprotein Testing, Rafai, Warnick and Dominiczak, eds. AACC Press, Washington, D.C.).

The skilled artisan would appreciate, based upon the disclosure provided herein, that the composition can encompass various other substances known in the art to be present in lipid and/or lipoprotein samples, such as, but not limited to, IDL, VLDL, chylomicrons and APO-E. Thus, the invention encompasses a composition comprising various components and subcomponents known in the art to be present in a lipid and/or lipoprotein sample, or a sample to be tested therefor.

Moreover, the invention is not limited to any particular value for any of the constituents present in the reference composition, nor to any particular combination of constituents. For instance, a reference composition of the invention can comprise of substantially pure CHOL, LDL, HDL, and triglycerides, or CHOL, LDL, HDL, triglycerides, APO-A and APO-B. Although some of these combinations of constituents, and known values therefor, are exemplified elsewhere herein, the invention is in no way limited to these, or any other, combinations of constituents or known values therefor. Rather, the various constituents can be used separately, or in combination with other useful constituents that are to be assayed for in a test sample, are also encompassed in the invention, and the invention is by no means limited to any constituent, combination of constituents, or particular known value thereof, and the exemplary reference compositions disclosed elsewhere herein are for illustrative purposes and do not limit the invention in any way.

In one embodiment, the substantially pure constituent is total cholesterol and the preferred known value ranges from about 0.0 to 5000, more preferably, from about 0.0 to 4000, even more preferably, from about 0.0 to 3000, and even more preferably, from about 0 to 2000 mg/dL. More preferably, the known value for CHOL in a reference composition of the invention ranges from about 0 to 1000 mg/dL, and most preferably, the value of CHOL ranges are the claimed analytical measurement range for the assay, and/or the established clinically reportable range of the constituent being assayed for as known in the art.

In another embodiment, the substantially pure constituent is LDL and the preferred known value ranges from about 0 to 5000, more preferably, from about 0 to 4000, even more preferably, from about 0 to 3000, yet more preferably, from about 0 to 2000, and even more preferably, from about 0 to 1000 mg/dL. More preferably, the known value for LDL in a reference composition of the invention ranges from about 0 to 500 mg/dL, and most preferably, the value of LDL ranges are the claimed analytical measurement range for the assay, and/or the established clinically reportable range for LDL as known in the art.

In another embodiment, the substantially pure constituent is triglycerides and the preferred known value ranges from about 0 to 4000, more preferably, from about 0 to 3000, even more preferably, from about 0 to 2000, yet more preferably, from about 0 to 1000, and even more preferably, from about 0 to 500 mg/dL. Most preferably, the known values for triglycerides in a reference composition of the invention ranges are the claimed analytical measurement range for the assay of interest and/or the established clinically reportable range for triglycerides as known in the art.

Furthermore, in another embodiment, the substantially pure constituent is HDL and the preferred known value ranges from about 0 to 1000, more preferably, from about 0 to 900, even more preferably, from about 0 to 800, yet more preferably, from about 0 to 700, and even more preferably, from about 0 to 600 mg/dL. More preferably, the known value for HDL in a reference composition ranges from about 0 to 500 mg/dL. Most preferably, the known values for HDL in a reference composition of the invention ranges are the claimed analytical measurement range for the assay of interest and/or the established clinically reportable range for HDL as known in the art.

The known constituent comprises substantially pure APO-A and the preferred known value ranges from about 0 to 1000, more preferably, from about 0 to 900, even more preferably, from about 0 to 800, yet more preferably, from about 0 to 700, and even more preferably, from about 0 to 600 mg/dL. More preferably, the known value for APO-A in a reference composition of the invention ranges from about 0 to 500 mg/dL, and most preferably, the value of APO-A ranges are the claimed analytical measurement range and/or the established clinically reportable range for APO-A as known in the art.

In addition, the substantially pure constituent is APO-B and the preferred known value ranges from about 0 to 1000, more preferably, from about 0 to 900, even more preferably, from about 0 to 800, yet more preferably, from about 0 to 700, and even more preferably, from about 0 to 600 mg/dL. Most preferably, the known value for APO-B in a reference composition of the invention ranges from about 0 to 500 mg/dL, and most preferably, the value of APO-B ranges are the claimed analytical measurement range and/or the established clinically reportable range for APO-B as known in the art.

In addition, the substantially pure constituent is Lp(a) and the preferred known value ranges from about 0 to 1000, more preferably, from about 0 to 900, even more preferably, from about 0 to 800, and yet more preferably, from about 0 to 700. Most preferably, the known value for Lp(a) in a reference composition of the invention ranges from about 0 to 640 mg/dL, and most preferably, the value of Lp(a) ranges are the claimed analytical measurement range and/or the established clinically reportable range for Lp(a) as known in the art.

The respective subcomponents of APO-A and APO-B may also be included. These substantially pure subcomponents may be, but are not limited to AII, AIV, B-48, B-100, CI, CII, CIII, D, E1, E2, E3, E4, E5, E6, F, G, H, and J, among others. The most preferred range of these subcomponents is about 0 to 500 mg/dL.

However, one skilled in the art would realize, based upon the disclosure provided herein, that a series of composition references, that is, at least two, can be used to generate a calibration curve such that each sample in a series comprises a range of known values relative to each other. Thus, the invention encompasses a series of reference compositions of the invention, comprising at least two different known value levels that are known such that the delta value between the two compositions can be used to calibrate the theoretical values for other reference compositions of different values. Therefore, the invention encompasses a kit comprising at least two reference compositions of different known values of a constituent of interest, where the delta between the two values is known as a calibration or calibration verification standard. Furthermore, the invention consists of various series of such reference compositions comprising a wide plethora of constituents, and combinations thereof, the only requirement is that the value of the constituent be known for each reference composition and such multi-level calibration verification and quality control sets are exemplified herein although the invention is not limited to these, nor to any other particular, sets of reference compositions.

Similarly, although a reference composition comprising a HEPES buffer system ranging in pH from about 6.5 to 8.0, the present invention is in no way limited to this, or any other, buffering system, or indeed, to any buffer. Thus, the skilled artisan would appreciate, once armed with the teachings provided herein, that a wide plethora of buffers can be used in the present invention, such as, but not limited to Good's Buffers, such as BES, MOPS, TES, Tris, Sorenson's Phosphate buffer, various physiological buffer systems, and the like. (See Tietz, 2000, In: *Fundamentals of Clinical Chemistry*, 5th ed., Burtis & Ashwood, eds., Elsevier Science Press, NY). Similarly, buffer systems are described in the website of Sigma-Aldrich, as listed in the area of interest encompassing biochemicals and reagents, more specifically, those set forth in the buffer explorer/buffer reference center portion of the website.

HEPES buffer comprises a buffer of known pH value ranging from about 6.5 to 9.0, even more preferably, from about 6.8 to 8.3, yet more preferably, from about 7.0 to 8.0. Most preferably, the known pH value for HEPES buffer in a reference composition of the invention ranges from about 7.3 to 7.5.

BES buffer comprises a known pH value ranging from about 6.5 to 9.0, yet more preferably, from about 6.8 to 8.3, even more preferably, from about 7.0 to 8.0. Most preferably, the known pH value for BES in a reference composition of the invention ranges from about pH 7.3 to 7.5.

MOPS buffer comprises a known pH value ranging from about 6.5 to 9.0 yet more preferably, from about 6.8 to 8.3, even more preferably, from about 7.0 to 8.0. Most preferably, a known pH value for MOPS in a reference composition of the invention ranges from about 7.3 to 7.5.

TES buffer comprises a known pH value ranging from about 6.5 to 9.0, yet more preferably, from about 6.8 to 8.3, even more preferably, from about 7.0 to 8.0. Most preferably, a known pH value for TES in a reference composition of the invention ranges from about 7.3 to 7.5.

TRIS buffer comprises a known pH value ranging from about 6.5 to 9.0, yet more preferably, from about 6.8 to 8.3, even more preferably, from about 7.0 to 8.0. Most preferably, the known pH value for TRIS in a reference composition of the invention ranges from about 7.3 to 7.5.

Sorenson's Phosphate buffer comprises a known pH value ranging from about 6.5 to 9.0, yet more preferably, from about 6.8 to 8.3, even more preferably, from about 7.0 to 8.0. Most preferably, the known pH value for Sorenson's Phosphate in a reference composition of the invention ranges from about 7.3 to 7.5.

As would be understood by one skilled in the art, the reference composition of the invention can, but need not, comprise an anti-microbial. An example of such an anti-microbial includes, but is not limited to, sodium azide and PROCLIN. The invention is not limited to these, or any other anti-microbials. Rather, numerous anti-microbials, both known and to be developed in the future, and the effective amount to be used thereof, can be used in the present invention. Many anti-microbials, including, but not limited to, those set forth in U.S. Pat. No. 5,891,734, are well-known in the art and are therefore not recited herein.

An anti-microbial of the invention is sodium azide. Preferably, the amount of sodium azide is less than about 0.09% based on weight per volume (w/v). The preferred amount of sodium azide is about 0.9 g/L.

Alternatively, the amount of PROCLIN ranges from about 10 ppm to about 100 ppm, even more preferably, from about 20 ppm about 80 ppm, yet more preferably, the amount ranges from about 30 ppm to about 60 ppm, and most preferably, the amount of PROCLIN is about 40 ppm. (See, e.g., Supelco Bulletin No. 900).

The reference composition may also include a secondary antioxidant such as, but not limited to, OXYRASE. As would be understood by the skilled artisan, based upon the disclosure provided herein, OXYRASE does not affect stability of a reference composition at a level of TDPA greater than about 9.0 grams per liter. Without wishing to be bound by any particular theory, it may be that OXYRASE requires a proton donor (e.g., lactic acid, and the like) to function as an oxygen scavenger. In addition, a composition comprising OXYRASE can, but needs not, comprise NaCl. TDPA may also be acting as a competitive inhibitor to OXYRASE, which at high concentrations, may reduce its effectiveness.

Preferably, the amount of OXYRASE ranges from about 0.05 U/mL to about 0.5 U/mL, even more preferably, from about 0.1 U/mL about 0.4 U/mL, yet more preferably, the amount ranges from about 0.1 U/mL to about 0.3 U/mL. Most preferably, the amount of OXYRASE is 0.1 U/mL. (See, e.g., U.S. Pat. No. 4,476,224; U.S. Pat. No. 4,996,073; and U.S. Pat. No. 5,240,851).

One of ordinary skill in the art, based upon the disclosure provided herein, would understand that the reference composition of the invention is preferably provided as an aqueous solution that is not, but can be, diluted to adjust the known value of at least one known constituent. Thus, the composition does not require reconstitution to produce an aqueous solution, thereby decreasing handling errors and costly manipulations thus providing a significant improvement over reference compositions that are provided in lyophilized and/or dry or powdered form which requires that liquid be added before the composition can be used. Therefore, the invention provides a stable aqueous or serum/plasma matrix reference composition that does not require reconstitution and/or the addition of any liquid before it can be used yet remains stable for a significant period of time.

II. Methods for Producing a Reference Composition

The invention includes a method for producing a reference composition comprising a substantially pure constituent of known value and a stabilizing amount of TDPA. The method comprises of an aqueous or protein base buffer matrix to which antioxidants and antimicrobials are added. After dissolution, the solution is then brought to the quantity sufficient (qs), and then filtered through, for instance, 0.2 μm filter. A component (i.e., an analyte), such as, but not limited to CHOL, HDL, LDL, and the like, is added at its desired targeted amount. The solution is then re-filtered. The reference composition is assayed on the applicable chemical analyzer for which it is made, to ensure the target concentration is achieved. If necessary, adjustments are made and the sample is re-assayed.

The invention encompasses a method for producing a stable control or calibration standard composition. The method comprises of admixing an aqueous or serum/plasma matrix solution with a stabilizing amount of 3,3'-thiodipropionic acid and a predetermined amount of a substantially pure analyte.

One skilled in the art would appreciate, based upon the disclosure provided herein, that a wide plethora of aqueous solutions can be used to produce the standard of the invention. Such aqueous solutions include, but are not limited to water, human plasma, human serum, a solution comprising bovine serum albumin, and a solution comprising human serum albumin, among many others. Such solutions are well-known in the art and are not discussed further herein.

III. Methods for Using a Reference Composition

The invention further includes a method for calibration or quality control of an instrument adapted to determine the amount of a constituent in a test solution. That is, as demonstrated by the data disclosed herein, the present invention demonstrates a method for using the reference composition of the invention to calibrate and/or verify and/or provide quality control for an instrument used to assess the amount of a constituent of interest in a sample.

The skilled artisan would appreciate, based upon the teachings provided herein, that the invention is not limited to any particular instrument, but rather the invention encompasses a wide plethora of instruments as are known in the art or to be developed in the future. That is, such instruments for assaying the presence and/or level of a known constituent of interest in a sample include, but are not limited to, multi-channel chemistry analyzers such as, for instance, the CX model and/or LX model from Beckman Coulter (Fullerton, Calif.), the Hitachi and Integra systems from Roche Diagnostics (Manheim, Germany), the Centaur, IMS and Advia systems from Bayer Healthcare (Tarrytown, N.Y.), the Aeroset and Chem 8000 systems from Abbott Diagnostics (Abbott Park, Ill.), the Vitros and DT systems from Ortho's J&J Clinical Diagnostics (Raritan, N.J.), the Dimension series from Dade Behring (Newark, Del.), and Dade Behring Limited (U.K.), the Polychem from Polymedco (Cortlandt Manor, N.Y.), the ATAC from Elan Diagnostics (Morristown, N.J. and Dublin, Ireland), and many others. Thus, the skilled artisan would understand, based upon the disclosure provided herein, that the invention is not limited in any way to any particular instrument, either known or to be developed used to examine a sample with respect to a reference composition of the invention. Such instruments, including serum analyzers, hand-held devices, single test devices, and the like, are well-known in the art and are not discussed further herein.

As will be understood by one of skill in the art, when armed with the disclosure set forth herein, a reference composition of the invention can be used to calibrate an instrument and/or an assay. That is, reference compositions and methods of the present invention are useful for calibration, calibration verification, quality control and linearity testing, among other uses.

The skilled artisan will know, based on the present disclosure, that a composition of the invention may be modified based on the needs of a particular application. By way of a non-limiting example, a particular antioxidant may be excluded from a reference composition if the antioxidant has the potential to interfere with the assay or with one or more other components of the reference composition. Similarly, the skilled artisan will know, based on the present disclosure, that a method of the invention may be modified based on the needs of a particular application. By way of a non-limiting example, a reference composition may be used in a two-point calibration assay. In another embodiment of the invention, a reference composition may be used in a five-point calibration assay. In one aspect, a reference composition may include as many or as few reference points as determined to be necessary to establish a valid and accurate reference curve.

There are numerous calibration schemes used in the clinical laboratory. Older methods, often manually performed, employ several concentration levels throughout the assay range and typically plot the recovery versus concentration or use linear regression to calculate patient analyte values. These methods can still be used. However, with the increasing use and availability of computer technology, methods that demonstrate linear performance now often use one or two calibrator points to achieve the same results. Quite often, the one or two set point method incorporates a saline or distilled water blank as an additional set point, this latter function being dictated by the instrument or reagent manufacturer. For non-linear chemistries, the traditional approach provides five or six levels of calibrator, usually set in a non-linear fashion dictated by the mathematical model used in the final calculation of patient result. A more recent trend for non-linear chemistries is to use one calibrator containing the highest concentration of analyte measured in the assay. Using this method, the analytical system is then directed to perform the necessary dilutions of this high concentration value to generate the predetermined calibration set points on the fly when the system calibrates the analyte.

Therefore, in an aspect of the present invention, a method features the use of multiple calibrator points in order to generate a reference curve. In one embodiment, a method features the use of more than one point. In another embodiment, one of the multiple points is a zero point. In yet another embodiment, the zero point is not included as one of the multiple points, but may be included separately in a reference curve. In another aspect of the present invention, a method features the use of a single calibration point, as described in detail elsewhere herein. In one embodiment, a method features the use of a zero point in addition to a single calibration point.

By way of a series of non-limiting examples, a method of the invention can use a reference curve based on a single concentration for calibration, a method of the invention can use a reference curve based on a single concentration plus a zero concentration point for calibration, a method of the invention can use a reference curve based on at least two concentrations for calibration, and a method of the invention can use a reference curve based on at least two concentrations plus a zero concentration point for calibration. In one aspect of the invention, the concentration of a calibration sample is known. In another aspect of the invention, the concentration of a calibration sample is not known. In yet another aspect of the invention, the concentration of at least one calibration sample in a mixture containing at least two calibration samples is known.

IV. Kits

The invention includes various kits which comprise a novel stable aqueous or serum/plasma matrix lipid standard of the invention, an applicator, and instructional materials which describe use of the kit to perform the methods of the invention. Although exemplary kits are described below, the contents of other useful kits will be apparent to the skilled artisan in light of the present disclosure. Each of these kits is included within the invention.

In one aspect, the invention includes a kit for calibration or quality control of an instrument adapted to determine the amount of a constituent in a test solution. The kit comprising a reference composition which comprises a known amount of a constituent and a stabilizing amount of 3,3'-thiodipropionic acid. The kit is further comprised of an applicator and instructional material for the use of the kit.

The kit is used pursuant to the methods disclosed in the invention. Briefly, the kit may be used to calibrate or verify calibration and/or for quality control purposes. This is because, as more fully disclosed elsewhere herein, the data disclosed herein demonstrates that addition of TDPA detectably stabilizes an aqueous lipid reference composition and provides a stable reference composition that can be used for, among other things, calibration and quality control in an assay and to assess the presence and/or concentration of a constituent of interest.

The kit further comprises of an applicator useful for administering the stable standard for use in the relevant assay. The particular applicator included in the kit will depend on, e.g., the method used assay a lipid, as well as the particular analyzer equipment used, and such applicators are well-known in the art and may include, among other things, a pipette, a syringe, a dropper bottle, and the like. Moreover, the kit comprises an instructional material for the use of the kit. These instructions simply embody the disclosure provided herein.

The kit includes a kit comprising the various combinations of constituents in various known amounts as disclosed elsewhere herein, including, but not limited to, one or more antioxidants, and one or more biological buffers. The composition is provided in an appropriate amount as set forth elsewhere herein.

Further, the kit includes a kit comprising a combination of at least two reference compositions comprising different known values of a known constituent such that the delta, or difference, between the two compositions is known. Such kits can be used to standardize or calibrate an instrument, for quality control purposes, and to produce a calibration curve for an instrument as discussed elsewhere herein. Thus, the invention encompasses a kit comprising of at least two reference compositions. While the invention is not limited to any particular set, certain combinations of reference compositions are exemplified elsewhere herein.

Additionally, the invention encompasses a kit comprising 3,3'-thiodipropionic acid, where the kit comprises at least one constituent, or analyte, the value for which is known. That is, the kit further comprises an analyte including, but not limited to, total cholesterol, LDL, HDL, triglycerides, APO-A, APO-B, Lp(a) and the like, and any combination thereof, as would be appreciated by one skilled in the art based upon the disclosure provided herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Multi-Point Calibrator Set

Table 1 demonstrates a configuration that uses the present invention at multiple levels for a multi-point calibration scheme for methods that require multiple set points for calibration. Several commercial methods utilize multi-point calibration for the components involved. These set points are designed to cover the full analytical measurement range.

TABLE 1

Multi-Point Calibrator Set

| Calibrator | Units | Set Point 1 | Set Point 2 | Set Point 3 | Set Point 4 | Set Point 5 |
|---|---|---|---|---|---|---|
| Total Cholesterol | mg/dL | 10 | 200 | 400 | 600 | 800 |
| HDL | mg/dL | 5 | 37.5 | 115 | 177.5 | 200 |
| Triglycerides | mg/dL | 0 | 250 | 500 | 750 | 1000 |
| LDL | mg/dL | 5 | 162.5 | 285 | 422.5 | 600 |
| APO A | mg/dL | 15.6 | 117.2 | 359.4 | 554.7 | 625 |
| APO B | mg/dL | 3.3 | 106.9 | 187.5 | 287.0 | 394.7 |

The various compositions were prepared as follows. Briefly, one liter of the matrix buffer for the calibrator set is produced as follows: 25 g (2.5% w/v) human serum albumin (HSA; Seracare Catalog No. HS430, 20 g (2.0% w/v) human gamma globulin (HGG; Seracare Catalog No. HS475, or equivalent), 34.42 g HEPES sodium (approximately 0.1M) (Sigma Catalog No. H7006, or equivalent), 6.4284 g (approximately 8 mM) sodium chloride (Sigma Catalog No. S9888, or equivalent), 4.0 g (about 50 mM) TDPA (Aldrich Catalog No. T3020-1, or equivalent), 2.242 g (about 10 mM) sodium lactate (Sigma Catalog No. L7022, or equivalent), 0.90 g (about 0.01 M) sodium azide (Sigma Catalog No. S8032, or equivalent), and 1.33 mL PROCLIN 300 (about 40 ppm) (Supelco Catalog No. 4-8127). Once dissolved, the pH was adjusted to 7.3-7.5, preferably, to about 7.4, using 1N HCl or 3N NaOH. The solution was made to the quantity sufficient. The solution was then 0.2 μm filtered using a Sartobran P Capsule (Sartorius Part No. 5231307H5, or equivalent).

The set points are prepared individually or from a dilution of the level 5 set point. In this instance, a linear relationship exists between calibrator set points and would be representative of a traditional manual chemistry assay where concentrations of the standard appear throughout the reportable range of the assay. This example can also be designed for a non-linear chemistry, in which instance, a level 5 set point is used to set the upper limit or mathematical boundary and additional set points are added throughout the assay range at such concentrations that an optimal curve shape and subsequent mathematical model can be established to permit calculation of clinical results.

Substantially pure lipid concentrates (Lee Cat. No. 361-10, 360-10, or equivalent) are diluted to the analytical range of the method and are assayed on the appropriate instrument. A value is assigned to the concentrated stock. An appropriate dilution is then made of the HDL and LDL stocks to obtain the desired set point value. For example, if the Total Cholesterol concentrated stock is at 4000 mg/dL, then a 1:5 is made in the matrix buffer to produce set point #5. This is done for each set point, if the points are prepared individually.

APO-A is a subcomponent of HDL, while APO-B is a subcomponent of LDL. The values obtained for these constituents are therefore dependent on the values for HDL and LDL. For example, a level 5 set point generated an HDL value of 118.7 mg/dL. The APO-A value obtained was 369.34 mg/dL. For the same sample, an LDL value of 510.2 mg/dL was produced, while its corresponding APO-B value was 335.3 mg/dL. Alternatively, APO-A and APO-B targets can be set with the resulting HDL and LDL values being dependent on the targeted apolipoprotein concentration.

Each level is then assayed. Adjustments are made to ensure that the targeted concentration is achieved. The sets are re-assayed and once the correct concentrations are achieved, the various levels are 0.2 µm filtered. These calibrators can be run and standardized against the designated reference method, such as the IFCC SP1-01 reference preparation for APO A-1, to establish a reference value as described in, e.g., Roche Product Insert APO A-1 version 2.0, February 2002. Once established, the end user can use the set points to calibrate a clinical analyzer. The compositions demonstrate extended stability compared with otherwise identical compositions that do not comprise TDPA.

Example 2

Two Point Calibrator Set

Table 2 demonstrates a configuration that uses two points for a two point calibration scheme for methods designed to be calibrated with a two level set points. Often, saline or another suitable blank material is used for one set point containing "zero" amount of the desired component.

TABLE 2

Two Point Calibrator Set

| Calibrator | Units | "Zero" Set Point | Set Point |
|---|---|---|---|
| Total Cholesterol | mg/dL | 0 | 200 |
| HDL | mg/dL | 0 | 60 |
| Triglycerides | mg/dL | 0 | 250 |
| LDL | mg/dL | 0 | 140 |
| APO A | mg/dL | 0 | 188 |
| APO B | mg/dL | 0 | 92 |

Using the buffer set forth previously relating to Table 1, substantially pure lipid concentrates are diluted and assayed on the appropriate instrument. A value is then assigned to the concentrated stock. An appropriate dilution is then made of the lipid stocks to obtain the desired set point value. The appropriate amount of triglycerides, HDL and LDL concentrates are added and dissolved. Once again, APO-A and APO-B are subcomponents of these constituents. The solutions are assayed and any necessary adjustments are made to ensure the set point is met. The samples are then re-tested and 0.2 µm filtered. The set point can be run against a reference method for value assignment, similar to as described with respect to the compositions set forth in Table 1. Once established, then end user can use the two set points to calibrate their clinical analyzers. The compositions demonstrate extended stability compared with otherwise identical compositions that do not comprise TDPA.

Example 3

Additional Two-Point Calibration Experiments

A two-point HDL mock calibrator was made to mimic the Beckman Lipid Calibrators on the Beckman CX7. The calibrators were made using a formulation for a lipid product, wherein analytes were added to buffer at desired analyte concentrations as set forth in detail elsewhere herein, including, for example, as set forth in Example 1. Concentrations of analytes were adjusted to meet the 2 required set points. Forty patient samples were obtained for lipid analysis and were analyzed following a modified EP9 Protocol. The CX7 was calibrated using the Beckman Lipid Calibrators. Patient samples were run in duplicate in groups of 5-6 samples per run. There were approximately 2 hours in-between calibrations. The instrument was recalibrated using mock calibrators and the same patient samples were run in duplicate. A total of 40 samples were run.

An examination of the statistical data reveals whether the calibrators were equivalent. If the t Stat<t critical two-tail (95%) then the calibrators show equivalency. In the case of HDL on the CX7 equivalency was shown.

In this mock calibrator study, the instrument manufacturer's calibration was used to establish the value of the mock calibrator set point. For a typical commercial product, the set point would be determined with a NIST reference material, according to national standards guidelines.

In an additional study, a single-point CHOL mock calibrator was made to mimic the Roche CFAS (Calibrator for Automated Systems) Calibrator on the Integra 400. The calibrator was made using a formulation for a lipid product as described elsewhere herein, and adjusted to meet the required set point. Forty patient samples were obtained for lipid analysis and were analyzed following a modified EP9 Protocol. The I400 was calibrated using the Roche CFAS Calibrator. Patient samples were run in duplicate in groups of 5-6 samples per run. Approximately 2 hours lapsed in-between calibrations. The instrument was re-calibrated using the mock calibrator and the same patient samples were run in duplicate. A total of 40 samples were run.

An examination of the statistical data reveals whether the calibrators were equivalent. The results were analyzed, in part, using a Student's T-test for results with equal variance. If the t Stat<t critical two-tail (95%), then the calibrators show equivalency. In the case of CHOL on the 1400, equivalency was shown.

In this mock calibrator study, the instrument manufacturer's calibration was used to establish the value of the set point used in the calibration. For a typical commercial product, the set point would be determined with a NIST reference material, according to national standards guidelines.

TABLE 3

Statistics for an HDL mock calibrator using the Beckman CX7.

| | HDL - 2 Calibration points | |
|---|---|---|
| Descriptive Statistics: | Test | Comparative |
| Mean | 45.25 | 42.70125 |
| Median | 42.65 | 40.3 |
| Mode | 41.9 | 40.5 |
| SD | 11.154655 | 10.6735743 |
| CV | 24.6511714 | 24.9959294 |
| Max | 88.1 | 80.5 |
| Min | 30.6 | 27.4 |
| Range | 57.5 | 53.1 |
| X − 2SD | 22.9406899 | 21.3541014 |
| X + 2SD | 67.5593101 | 64.0483986 |
| n | 80 | 80 |
| Duplicates | 40 | 40 |
| T = 1.03621111 * C + 1.00249024 | | |
| r = 0.9915495 | | |
| r2 = 0.98317041 | | |
| Sy/x = 1.47442215 | | |

X = Mean
SD = Standard Deviation of the sample
CV = Coefficient of variation
Test = 1.03621111 * Comparative + 1.00249024
r = coefficient of correlation
r$^2$ = coefficient of determination
Sy/x = standard error of the estimate

TABLE 4

Observed Data Based on Experimental Subjects, Using HDL Analyte and Lipid Calibration Reference

| | Test | | Comparative | | | |
|---|---|---|---|---|---|---|
| Sample # | Repli-cate 1 | Repli-cate 2 | Repli-cate 1 | Replicate 2 | Test Mean | Comparative Mean |
| 1 | 41.9 | 41.9 | 41.5 | 40.5 | 41.9 | 41 |
| 2 | 63.8 | 62.8 | 62.3 | 62.7 | 63.3 | 62.5 |
| 3 | 36.8 | 37 | 37.4 | 35.9 | 36.9 | 36.65 |
| 4 | 62.5 | 62 | 62.5 | 62.1 | 62.25 | 62.3 |
| 5 | 32.5 | 31.1 | 27.4 | 27.5 | 31.8 | 27.45 |
| 6 | 87.6 | 88.1 | 80.5 | 79.2 | 87.85 | 79.85 |
| 7 | 48.3 | 46.2 | 39.9 | 39.3 | 47.25 | 39.6 |
| 8 | 42.5 | 43.1 | 40.8 | 39.9 | 42.8 | 40.35 |
| 9 | 41.1 | 40.7 | 38.5 | 39.7 | 40.9 | 39.1 |
| 10 | 37.9 | 37.1 | 36.2 | 36.2 | 37.5 | 36.2 |
| 11 | 42.8 | 41.9 | 41.3 | 40.5 | 42.35 | 40.9 |
| 12 | 31.1 | 31.2 | 29.5 | 29.5 | 31.15 | 29.5 |
| 13 | 42.9 | 42.8 | 41.2 | 40.1 | 42.85 | 40.65 |
| 14 | 33.2 | 33.4 | 31.4 | 31.1 | 33.3 | 31.25 |
| 15 | 41.5 | 41.6 | 38.9 | 39.4 | 41.55 | 39.15 |
| 16 | 31.2 | 30.6 | 28.8 | 29.1 | 30.9 | 28.95 |
| 17 | 44.2 | 43.3 | 41.9 | 42.3 | 43.75 | 42.1 |
| 18 | 44.8 | 43.8 | 41.8 | 41.1 | 44.3 | 41.45 |
| 19 | 33 | 32.7 | 30.6 | 30.1 | 32.85 | 30.35 |
| 20 | 42.2 | 41.7 | 39.6 | 39.5 | 41.95 | 39.55 |
| 21 | 40.7 | 40.6 | 37.9 | 38.3 | 40.65 | 38.1 |
| 22 | 58.4 | 57.2 | 54.5 | 55.1 | 57.8 | 54.8 |
| 23 | 34.2 | 33.3 | 31.5 | 31.4 | 33.75 | 31.45 |
| 24 | 58.8 | 59.1 | 56.5 | 57.8 | 58.95 | 57.15 |
| 25 | 41.7 | 42.2 | 39.4 | 39.2 | 41.95 | 39.3 |
| 26 | 53.6 | 51.4 | 48.7 | 49.7 | 52.5 | 49.2 |
| 27 | 41.3 | 40.9 | 38 | 37.7 | 41.1 | 37.85 |
| 28 | 53.9 | 53.7 | 50.4 | 50.2 | 53.8 | 50.3 |
| 29 | 42.6 | 42 | 40.2 | 39.6 | 42.3 | 39.9 |
| 30 | 44.8 | 45.2 | 42.9 | 40.9 | 45 | 41.9 |
| 31 | 43.3 | 42.7 | 40.4 | 41.1 | 43 | 40.75 |
| 32 | 51.8 | 51.6 | 49.2 | 49.8 | 51.7 | 49.5 |
| 33 | 34.1 | 34.3 | 32 | 31.6 | 34.2 | 31.8 |
| 34 | 59.8 | 58.6 | 55.4 | 55.3 | 59.2 | 55.35 |
| 35 | 44.6 | 44.9 | 42.1 | 42.1 | 44.75 | 42.1 |
| 36 | 49 | 49.5 | 46.1 | 46.6 | 49.25 | 46.35 |
| 37 | 59.3 | 60.2 | 56.9 | 57.2 | 59.75 | 57.05 |
| 38 | 48.6 | 47.9 | 46.5 | 45.3 | 48.25 | 45.9 |
| 39 | 37.3 | 37.9 | 34.8 | 35.4 | 37.6 | 35.1 |
| 40 | 37.5 | 36.7 | 35.3 | 35.4 | 37.1 | 35.35 |

TABLE 5

Statistics for a CHOL mock calibrator using the Integra 400.

| | CHOL | |
|---|---|---|
| Descriptive Statistics: | Test | Comparative |
| Mean | 202.1525 | 194.7875 |
| Median | 199.4 | 192.15 |
| Mode | 197.3 | 180.3 |
| SD | 47.7276131 | 46.334473 |
| CV | 23.6097071 | 23.7871901 |
| Max | 321.9 | 310.1 |
| Min | 106.1 | 101.4 |
| Range | 215.8 | 208.7 |
| X − 2SD | 106.697274 | 102.118554 |
| X + 2SD | 297.607726 | 287.456446 |
| n | 80 | 80 |
| Duplicates | 40 | 40 |
| T = 1.02966092 * C + 1.5874244 | | |
| r = 0.99925842 | | |
| r2 = 0.99851739 | | |
| Sy/x = 1.87336112 | | |

(Statistical terms defined elsewhere herein)

TABLE 6

Observed Data Based on Experimental Subjects, Using CHOL Analyte and CFAS Calibration Reference

| | Test | | Comparative | | | |
|---|---|---|---|---|---|---|
| Sample # | Repli-cate 1 | Repli-cate 2 | Repli-cate 1 | Replicate 2 | Test Mean | Comparative Mean |
| 1 | 106.1 | 106.2 | 101.4 | 102.7 | 106.15 | 102.05 |
| 2 | 157.4 | 160.8 | 153.7 | 157.7 | 159.1 | 155.7 |
| 3 | 217.7 | 218.4 | 208.1 | 213.6 | 218.05 | 210.85 |
| 4 | 132 | 131.7 | 126.1 | 128.4 | 131.85 | 127.25 |
| 5 | 197.3 | 199.1 | 189.8 | 194.5 | 198.2 | 192.15 |
| 6 | 305.9 | 307.9 | 293.8 | 307 | 306.9 | 300.4 |
| 7 | 133 | 133.7 | 127.3 | 130.2 | 133.35 | 128.75 |
| 8 | 199.7 | 200.4 | 191.5 | 192.8 | 200.05 | 192.15 |
| 9 | 229 | 230.7 | 219.2 | 218 | 229.85 | 218.6 |
| 10 | 241.1 | 239.7 | 229.6 | 228.6 | 240.4 | 229.1 |
| 11 | 171.4 | 171.7 | 165.4 | 164.6 | 171.55 | 165 |
| 12 | 212.9 | 212.1 | 204 | 200.8 | 212.5 | 202.4 |
| 13 | 180.9 | 179.1 | 171.9 | 171.1 | 180 | 171.5 |
| 14 | 204.8 | 205 | 196.5 | 196.2 | 204.9 | 196.35 |
| 15 | 228.3 | 225.7 | 216.3 | 215.9 | 227 | 216.1 |
| 16 | 235.2 | 234.4 | 227.4 | 226.6 | 234.8 | 227 |
| 17 | 181.4 | 183 | 174.7 | 173.2 | 182.2 | 173.95 |
| 18 | 169 | 169.1 | 161.5 | 160.8 | 169.05 | 161.15 |
| 19 | 210.1 | 209.6 | 201.7 | 202 | 209.85 | 201.85 |
| 20 | 321.8 | 321.9 | 310.1 | 308.7 | 321.85 | 309.4 |
| 21 | 130.3 | 130 | 125.8 | 124.6 | 130.15 | 125.2 |
| 22 | 287.6 | 287.7 | 277.4 | 274.7 | 287.65 | 276.05 |
| 23 | 141.3 | 141.5 | 137.5 | 137.1 | 141.4 | 137.3 |
| 24 | 218.5 | 217.8 | 211.6 | 208.8 | 218.15 | 210.2 |
| 25 | 262.4 | 262.7 | 254.2 | 253.9 | 262.55 | 254.05 |
| 26 | 187.1 | 186.5 | 182.7 | 180.3 | 186.8 | 181.5 |
| 27 | 205.6 | 207.5 | 205.2 | 200.9 | 206.55 | 203.05 |
| 28 | 232.3 | 231.2 | 224.6 | 223.3 | 231.75 | 223.95 |
| 29 | 191.9 | 192 | 188.7 | 186.6 | 191.95 | 187.65 |
| 30 | 201.3 | 202.9 | 196.3 | 195.4 | 202.1 | 195.85 |
| 31 | 153.3 | 159.9 | 145.8 | 147.6 | 156.6 | 146.7 |
| 32 | 180.2 | 184.3 | 173.8 | 173.8 | 182.25 | 173.8 |
| 33 | 207.1 | 205.9 | 199.2 | 199.2 | 206.5 | 199.2 |
| 34 | 197.3 | 197.7 | 189.9 | 190.9 | 197.5 | 190.4 |
| 35 | 245.7 | 246.7 | 237.3 | 237.7 | 246.2 | 237.5 |
| 36 | 174.5 | 174.3 | 168.8 | 169.1 | 174.4 | 168.95 |
| 37 | 153.4 | 153.4 | 148 | 146.2 | 153.4 | 147.1 |
| 38 | 287.8 | 289.1 | 281.8 | 279.1 | 288.45 | 280.45 |
| 39 | 197.5 | 196.6 | 190.2 | 190.1 | 197.05 | 190.15 |
| 40 | 186.7 | 187.5 | 181.2 | 180.3 | 187.1 | 180.75 |

Example 4

Multi-Constituent Two-Point Calibration

Multi-constituent mock calibrators were made to mimic the CFAS Lipids Roche calibrator for HDL, LDL, and TRIG on the Hitachi 911 and for APOA and APOB on the Integra 400. The calibrators were made using the formulation for a lipid product as described elsewhere herein, and adjusted the targets to meet the required set point for each analyzer. Forty patient samples were obtained for lipid analysis and were analyzed following a modified EP9 Protocol. Both the 911 and 1400 were calibrated using the Roche CFAS Lipid Calibrator. Patient samples were run in duplicate in groups of 5-6 samples per run. There were approximately 2 hours in-between calibrations. The instrument was re-calibrated using the mock calibrators and the same patient samples were run in duplicate. A total of 40 samples were run.

An examination of the statistical data reveals whether the calibrators were equivalent. If the t Stat<t critical two-tail (95%) then the calibrators show equivalency. In the case of HDL, LDL, and TRIG on the 911 equivalency was shown. In the case of APOA on the 1400 equivalency was shown.

In the case of APOB on the 1400 equivalency was not shown. This would suggest that if the error was increased to 99% confidence, then equivalency may be achieved.

In this mock calibrator study, the instrument manufacturer's calibration was used to establish the value of the mock calibrator set point. For a typical commercial product, the set point would be determined with a NIST reference material.

TABLE 7

Statistics for an HDL mock calibrator using the Hitachi 911.

| Descriptive Statistics: | HDL Test | Comparative |
|---|---|---|
| Mean | 50.325 | 49.03 |
| Median | 46.41 | 44.645 |
| Mode | 52.58 | 43.4 |
| SD | 14.6395963 | 14.7279808 |
| CV | 29.0901069 | 30.0387126 |
| Max | 96.19 | 95.7 |
| Min | 26.51 | 27.17 |
| Range | 69.68 | 68.53 |
| X − 2SD | 21.0458074 | 19.5740384 |
| X + 2SD | 79.6041926 | 78.4859616 |
| n | 80 | 80 |
| Duplicates | 40 | 40 |
| T = 0.99012578 * C + 1.77913289 | | |
| r = 0.99613133 | | |
| r2 = 0.99227763 | | |
| Sy/x = 1.31107401 | | |

(statistical terms defined elsewhere herein)

TABLE 8

Observed Data Based on Experimental Subjects, Using HDL Analyte and CFAS Lipid Calibration Reference

| | Test | | Comparative | | | |
|---|---|---|---|---|---|---|
| | Replicate 1 | Replicate 2 | Replicate 1 | Replicate 2 | Test Mean | Comparative Mean |
| 1 | 44.46 | 45.82 | 42.49 | 43.57 | 45.14 | 43.03 |
| 2 | 68.9 | 68.67 | 69.09 | 67.28 | 68.785 | 68.185 |
| 3 | 38.76 | 38.8 | 38.28 | 38.71 | 38.78 | 38.495 |
| 4 | 66.67 | 66.52 | 64.84 | 65.47 | 66.595 | 65.155 |
| 5 | 95.17 | 96.19 | 95.19 | 95.7 | 95.68 | 95.445 |
| 6 | 86.38 | 84.87 | 84.76 | 84.25 | 85.625 | 84.505 |
| 7 | 43.67 | 43.89 | 43.4 | 44.26 | 43.78 | 43.83 |
| 8 | 45.15 | 45.64 | 44.73 | 44.67 | 45.395 | 44.7 |
| 9 | 42.96 | 43.4 | 42.76 | 43.4 | 43.18 | 43.08 |
| 10 | 39.92 | 39.09 | 38.69 | 38.57 | 39.505 | 38.63 |
| 11 | 45.09 | 45.29 | 43.32 | 44.22 | 45.19 | 43.77 |
| 12 | 33.82 | 34.1 | 34.22 | 32.9 | 33.96 | 33.56 |
| 13 | 47.14 | 46.35 | 45.52 | 45.84 | 46.745 | 45.68 |
| 14 | 36.02 | 35.03 | 34.31 | 34.17 | 35.525 | 34.24 |
| 15 | 44.49 | 44.81 | 41.79 | 41.92 | 44.65 | 41.855 |
| 16 | 34.06 | 34.19 | 31.05 | 31.53 | 34.125 | 31.29 |
| 17 | 48.5 | 49.43 | 45.5 | 46.16 | 48.965 | 45.83 |
| 18 | 46.88 | 47.91 | 44.33 | 44.62 | 47.395 | 44.475 |
| 19 | 35.08 | 34.6 | 32.38 | 32.26 | 34.84 | 32.32 |
| 20 | 47.12 | 47.32 | 44.97 | 44.74 | 47.22 | 44.855 |
| 21 | 44.82 | 44.85 | 42.59 | 42.8 | 44.835 | 42.695 |
| 22 | 61.25 | 62.1 | 57.23 | 58.43 | 61.675 | 57.83 |
| 23 | 38.25 | 37.5 | 35.52 | 35.67 | 37.875 | 35.595 |
| 24 | 63.68 | 64.57 | 60.35 | 60.64 | 64.125 | 60.495 |
| 25 | 45.71 | 46.26 | 42.82 | 42.66 | 45.985 | 42.74 |
| 26 | 52.58 | 51.57 | 51.49 | 52.09 | 52.075 | 51.79 |
| 27 | 66.19 | 67.08 | 62.94 | 64.43 | 66.635 | 63.685 |
| 28 | 52.58 | 54.68 | 51.79 | 52.89 | 53.63 | 52.34 |
| 29 | 34.56 | 34.84 | 35.17 | 34 | 34.7 | 34.585 |
| 30 | 46.47 | 45.63 | 44.45 | 43.69 | 46.05 | 44.07 |
| 31 | 47.85 | 46.78 | 45.99 | 46.09 | 47.315 | 46.04 |
| 32 | 56.99 | 56.28 | 55.08 | 54.56 | 56.635 | 54.82 |
| 33 | 40.75 | 40.01 | 39.05 | 40.17 | 40.38 | 39.61 |
| 34 | 61.74 | 62.57 | 60.9 | 61.82 | 62.155 | 61.36 |

TABLE 8-continued

Observed Data Based on Experimental Subjects, Using HDL Analyte and CFAS Lipid Calibration Reference

| | Test | | Comparative | | | |
|---|---|---|---|---|---|---|
| | Replicate 1 | Replicate 2 | Replicate 1 | Replicate 2 | Test Mean | Comparative Mean |
| 35 | 52.08 | 53.34 | 51.83 | 53.32 | 52.71 | 52.575 |
| 36 | 36.93 | 37.18 | 37.19 | 36.69 | 37.055 | 36.94 |
| 37 | 27.23 | 26.51 | 27.17 | 27.49 | 26.87 | 27.33 |
| 38 | 66.45 | 64.93 | 68.25 | 66.2 | 65.69 | 67.225 |
| 39 | 48.46 | 47.3 | 49.19 | 48.75 | 47.88 | 48.97 |
| 40 | 77.46 | 77.83 | 77.8 | 77.35 | 77.645 | 77.575 |

TABLE 9

Statistics for an LDL mock calibrator using the Hitachi 911.

| Descriptive Statistics | LDL Test | Comparative |
|---|---|---|
| Mean | 116.703605 | 113.616395 |
| Median | 109.17 | 106.305 |
| Mode | 106.91 | 103.95 |
| SD | 40.2646729 | 39.1815211 |
| CV | 34.5016532 | 34.4857984 |
| Max | 227.22 | 221.08 |
| Min | 46.84 | 46.48 |
| Range | 180.38 | 174.6 |
| X − 2SD | 36.1742588 | 35.2533532 |
| X + 2SD | 197.232951 | 191.979437 |
| n | 86 | 86 |
| Duplicates | 43 | 43 |
| T = 1.02737512 * C + −0.0230527 | | |
| r = 0.99970788 | | |
| r2 = 0.99941585 | | |
| Sy/x = 0.9906674 | | |

(statistical terms defined elsewhere herein)

TABLE 10

Observed Data Based on Experimental Subjects, Using LDL Analyte and CFAS Lipid Calibration Reference

| | Test | | Comparative | | | |
|---|---|---|---|---|---|---|
| | Replicate 1 | Replicate 2 | Replicate 1 | Replicate 2 | Test Mean | Comparative Mean |
| 1 | 204.2 | 205.78 | 200.82 | 200.62 | 204.99 | 200.72 |
| 2 | 111.48 | 110.9 | 108.96 | 107.64 | 111.19 | 108.3 |
| 3 | 76.05 | 76.16 | 75.12 | 75.2 | 76.105 | 75.16 |
| 4 | 137.68 | 135.16 | 133.68 | 132.1 | 136.42 | 132.89 |
| 5 | 109.29 | 104.61 | 105.3 | 105.06 | 106.95 | 105.18 |
| 6 | 116.07 | 115.26 | 113.43 | 114.05 | 115.665 | 113.74 |
| 7 | 128 | 129.48 | 125.38 | 125.44 | 128.74 | 125.41 |
| 8 | 109.05 | 107.87 | 106.08 | 106.53 | 108.46 | 106.305 |
| 9 | 125.67 | 124.77 | 122.55 | 123.9 | 125.22 | 123.225 |
| 10 | 98.71 | 96.72 | 96.99 | 95.84 | 97.715 | 96.415 |
| 11 | 107.14 | 107.48 | 103.04 | 103.95 | 107.31 | 103.495 |
| 12 | 63.42 | 63.39 | 61.93 | 61.96 | 63.405 | 61.945 |
| 13 | 118.28 | 117.95 | 116.41 | 113.05 | 118.115 | 114.73 |
| 14 | 107.91 | 106.91 | 103.95 | 104.27 | 107.41 | 104.11 |
| 15 | 106.34 | 105.48 | 104.33 | 103.98 | 105.91 | 104.155 |
| 16 | 76.08 | 75.67 | 73.89 | 72.85 | 75.875 | 73.37 |
| 17 | 94.94 | 94.55 | 92.9 | 91.65 | 94.745 | 92.275 |
| 18 | 151.47 | 150.94 | 146.47 | 147.24 | 151.205 | 146.855 |
| 19 | 107.32 | 106.8 | 103.01 | 101.26 | 107.06 | 102.135 |
| 20 | 126.31 | 127.18 | 122.11 | 121.3 | 126.745 | 121.705 |
| 21 | 129.17 | 129.72 | 126.05 | 124.92 | 129.445 | 125.485 |
| 22 | 108.16 | 106.24 | 103.15 | 102.81 | 107.2 | 102.98 |
| 23 | 109.55 | 111.03 | 107.61 | 108.62 | 110.29 | 108.115 |

TABLE 10-continued

Observed Data Based on Experimental Subjects, Using LDL Analyte and CFAS Lipid Calibration Reference

| | Test | | Comparative | | | |
|---|---|---|---|---|---|---|
| | Replicate 1 | Replicate 2 | Replicate 1 | Replicate 2 | Test Mean | Comparative Mean |
| 24 | 219.7 | 219.07 | 216.49 | 213.8 | 219.385 | 215.145 |
| 25 | 62.74 | 62.38 | 61.68 | 61.3 | 62.56 | 61.49 |
| 26 | 47.75 | 46.84 | 47.27 | 46.48 | 47.295 | 46.875 |
| 27 | 112.27 | 113.82 | 112.42 | 110.81 | 113.045 | 111.615 |
| 28 | 108.9 | 106.91 | 105.78 | 104.24 | 107.905 | 105.01 |
| 29 | 227.22 | 224.76 | 218.82 | 221.08 | 225.99 | 219.95 |
| 30 | 76.63 | 77.98 | 75 | 74.97 | 77.305 | 74.985 |
| 31 | 98.7 | 99.06 | 96.47 | 96.68 | 98.88 | 96.575 |
| 32 | 128.34 | 126.55 | 124.59 | 124.61 | 127.445 | 124.6 |
| 33 | 194.95 | 197.19 | 191.86 | 188.59 | 196.07 | 190.225 |
| 34 | 83.49 | 83.24 | 81.79 | 80.15 | 83.365 | 80.97 |
| 35 | 158.47 | 159.52 | 155.7 | 153.72 | 158.995 | 154.71 |
| 36 | 97.81 | 98.57 | 95.7 | 94.5 | 98.19 | 95.1 |
| 37 | 128.16 | 128.8 | 124.29 | 122.76 | 128.48 | 123.525 |
| 38 | 150.66 | 152.11 | 146.44 | 145.49 | 151.385 | 145.965 |
| 39 | 154.06 | 153.63 | 147.09 | 149.63 | 153.845 | 148.36 |
| 40 | 124.96 | 125.5 | 123.37 | 120.56 | 125.23 | 121.965 |
| 41 | 74.73 | 75.16 | 72.03 | 70.96 | 74.945 | 71.495 |
| 42 | 103.97 | 104.27 | 101.94 | 99.99 | 104.12 | 100.965 |
| 43 | 47.67 | 47.63 | 47.81 | 46.75 | 47.65 | 47.28 |

TABLE 11

Statistics for a TRIG mock calibrator using the Hitachi 911.

| | TRIG | |
|---|---|---|
| Descriptive Statistics: | Test | Comparative |
| Mean | 195.7775 | 191.37 |
| Median | 138.6 | 134.25 |
| Mode | 118.9 | #NA |
| SD | 194.022104 | 188.235364 |
| CV | 99.1033721 | 98.3620024 |
| Max | 1093.5 | 1026.6 |
| Min | 46.3 | 44.4 |
| Range | 1047.2 | 982.2 |
| X − 2SD | −192.26671 | −185.10073 |
| X + 2SD | 583.821709 | 567.840728 |
| n | 80 | 80 |
| Duplicates | 40 | 40 |
| T = 1.02983342 * C + −1.3017213 | | |
| r = 0.99916942 | | |
| r2 = 0.99833953 | | |
| Sy/x = 8.06009802 | | |

(statistical terms defined elsewhere herein)

TABLE 12

Observed Data Based on Experimental Subjects, Using TRIG Analyte and CFAS Lipid Calibration Reference

| Sample # | Test | | Comparative | | | |
|---|---|---|---|---|---|---|
| | Replicate 1 | Replicate 2 | Replicate 1 | Replicate 2 | Test Mean | Comparative Mean |
| 1 | 453.1 | 446.8 | 460.4 | 454.3 | 449.95 | 457.35 |
| 2 | 96.3 | 98.2 | 97 | 99.3 | 97.25 | 98.15 |
| 3 | 157.9 | 155.5 | 160.6 | 158 | 156.7 | 159.3 |
| 4 | 155.7 | 158.2 | 155.2 | 155.8 | 157.15 | 155.5 |
| 5 | 98.7 | 98.6 | 95.8 | 98.4 | 98.65 | 97.1 |
| 6 | 97.3 | 97.6 | 98.5 | 97.9 | 97.45 | 98.2 |
| 7 | 100.8 | 101.7 | 102 | 101.9 | 101.25 | 101.95 |
| 8 | 137.4 | 135.3 | 134.4 | 136.4 | 136.35 | 135.4 |
| 9 | 172.5 | 173.8 | 169.5 | 173.4 | 173.15 | 171.45 |

TABLE 12-continued

Observed Data Based on Experimental Subjects, Using TRIG Analyte and CFAS Lipid Calibration Reference

| Sample # | Test | | Comparative | | | |
|---|---|---|---|---|---|---|
| | Replicate 1 | Replicate 2 | Replicate 1 | Replicate 2 | Test Mean | Comparative Mean |
| 10 | 179.4 | 175.9 | 176.2 | 178.9 | 177.65 | 177.55 |
| 11 | 125.8 | 125.6 | 129 | 127.9 | 125.7 | 128.45 |
| 12 | 234 | 231.9 | 228.8 | 228.5 | 232.95 | 228.65 |
| 13 | 81 | 81.3 | 81.3 | 81.5 | 81.15 | 81.4 |
| 14 | 119.2 | 118.9 | 117.7 | 117 | 119.05 | 117.35 |
| 15 | 78.7 | 80.6 | 76.7 | 77.8 | 79.65 | 77.25 |
| 16 | 195.8 | 197.2 | 187.7 | 186.7 | 196.5 | 187.2 |
| 17 | 81.9 | 83.9 | 81 | 80.1 | 82.9 | 80.55 |
| 18 | 228.1 | 225.6 | 215.6 | 214.4 | 226.85 | 215 |
| 19 | 363.5 | 360.6 | 355.8 | 352.2 | 362.05 | 354 |
| 20 | 136.8 | 136.7 | 132.5 | 128.9 | 136.75 | 130.7 |
| 21 | 102.3 | 103.2 | 99.5 | 97.3 | 102.75 | 98.4 |
| 22 | 118.9 | 121 | 117.1 | 115.3 | 119.95 | 116.2 |
| 23 | 134.2 | 135.7 | 131.1 | 131.8 | 134.95 | 131.45 |
| 24 | 57.4 | 58.2 | 54.7 | 51.7 | 57.8 | 53.2 |
| 25 | 181 | 183.9 | 179.3 | 175.4 | 182.45 | 177.35 |
| 26 | 46.3 | 49 | 44.4 | 45.6 | 47.65 | 45 |
| 27 | 215.3 | 215.9 | 206.2 | 205.8 | 215.6 | 206 |
| 28 | 139.8 | 143.7 | 133.5 | 134.1 | 141.75 | 133.8 |
| 29 | 236 | 234.5 | 226.1 | 226.9 | 235.25 | 226.5 |
| 30 | 1072.2 | 1093.5 | 1024.8 | 1026.6 | 1082.85 | 1025.7 |
| 31 | 177.7 | 176.3 | 170.8 | 167.9 | 177 | 169.35 |
| 32 | 231.5 | 229.1 | 217.1 | 219.2 | 230.3 | 218.15 |
| 33 | 230 | 233.6 | 224 | 221.7 | 231.8 | 222.85 |
| 34 | 97 | 93.7 | 93.5 | 92.5 | 95.35 | 93 |
| 35 | 222.3 | 220.5 | 210.3 | 210.8 | 221.4 | 210.55 |
| 36 | 163.1 | 161 | 162 | 163.7 | 162.05 | 162.85 |
| 37 | 68 | 67 | 67.2 | 66.2 | 67.5 | 66.7 |
| 38 | 83.3 | 84 | 83.7 | 85.1 | 83.65 | 84.4 |
| 39 | 831.9 | 815.1 | 823.5 | 834.4 | 823.5 | 828.95 |
| 40 | 128.5 | 128.4 | 132.3 | 131.5 | 128.45 | 131.9 |

TABLE 13

Statistics for an APOA multi-constituent mock calibrator using the Integra 400.

| | APO-A | |
|---|---|---|
| Descriptive Statistics: | Test | Comparative |
| Mean | 152.97125 | 148.44125 |
| Median | 149.6 | 142.75 |
| Mode | 143 | 187.3 |
| SD | 22.8509047 | 24.44050743 |
| CV | 14.9380388 | 16.464768 |
| Max | 227.9 | 233.4 |
| Min | 111.8 | 108.6 |
| Range | 116.1 | 124.8 |
| X − 2SD | 107.269441 | 99.56023514 |
| X + 2SD | 198.673059 | 197.3222649 |
| N | 80 | 80 |
| Duplicates | 40 | 40 |
| T = 0.90586965 * C + 18.50282656 | | |
| R = 0.96613608 | | |
| r2 = 0.93341892 | | |
| Sy/x = 5.96187745 | | |

(statistical terms defined elsewhere herein)

TABLE 14

Observed Data Based on Experimental Subjects, Using APOA Analyte and CFAS Lipid Calibration Reference

| | Test | | Comparative | | | |
|---|---|---|---|---|---|---|
| Sample # | Replicate 1 | Replicate 2 | Replicate 1 | Replicate 2 | Test Mean | Comparative Mean |
| 1 | 152 | 147.1 | 155 | 143.9 | 149.55 | 149.45 |
| 2 | 196.7 | 195.3 | 194.5 | 185.9 | 196 | 190.2 |
| 3 | 150.6 | 143 | 135.4 | 132.4 | 146.8 | 133.9 |
| 4 | 189.9 | 194.1 | 184.6 | 187.3 | 192 | 185.95 |
| 5 | 227.9 | 221 | 233.4 | 219.1 | 224.45 | 226.25 |
| 6 | 116.4 | 111.8 | 118.7 | 108.6 | 114.1 | 113.65 |
| 7 | 189.3 | 200.3 | 188.7 | 196.2 | 194.8 | 192.45 |
| 8 | 133.4 | 135 | 133 | 128 | 134.2 | 130.5 |
| 9 | 141.8 | 150.7 | 147 | 139.7 | 146.25 | 143.35 |
| 10 | 140.4 | 149.1 | 140 | 150.1 | 144.75 | 145.05 |
| 11 | 150.7 | 143 | 150.3 | 134.5 | 146.85 | 142.4 |
| 12 | 151.4 | 145 | 147.5 | 142.4 | 148.2 | 144.95 |
| 13 | 122.9 | 114.3 | 117.5 | 125.2 | 118.6 | 121.35 |
| 14 | 153 | 147.7 | 150.2 | 154.1 | 150.35 | 152.15 |
| 15 | 119.6 | 123.7 | 129.7 | 130.7 | 121.65 | 130.2 |
| 16 | 144.7 | 143.1 | 133.2 | 125.7 | 143.9 | 129.45 |
| 17 | 123.7 | 125.2 | 114.2 | 110.3 | 124.45 | 112.25 |
| 18 | 135.2 | 149 | 127.6 | 128.7 | 142.1 | 128.15 |
| 19 | 166 | 157 | 144.8 | 148 | 161.5 | 146.4 |
| 20 | 134.9 | 132.5 | 123.2 | 123.2 | 133.7 | 123.2 |
| 21 | 155.2 | 161 | 143.2 | 143 | 158.1 | 143.1 |
| 22 | 148.6 | 145.8 | 139.6 | 137.7 | 147.2 | 138.65 |
| 23 | 174.4 | 171.9 | 166.6 | 168.7 | 173.15 | 167.65 |
| 24 | 125.9 | 133.6 | 114.3 | 119.7 | 129.75 | 117 |
| 25 | 154.8 | 156.9 | 151.4 | 154.4 | 155.85 | 152.9 |
| 26 | 145.3 | 147.5 | 141.5 | 138.8 | 146.4 | 140.15 |
| 27 | 150.5 | 149 | 141.8 | 141 | 149.75 | 141.4 |
| 28 | 148.6 | 148.4 | 141.8 | 142.5 | 148.5 | 142.15 |
| 29 | 188.3 | 184.8 | 189.3 | 183.7 | 186.55 | 186.5 |
| 30 | 152.8 | 154.7 | 145.5 | 141.7 | 153.75 | 143.6 |
| 31 | 149.6 | 145.2 | 140.1 | 137.8 | 147.4 | 138.95 |
| 32 | 156.9 | 148.9 | 146.8 | 147.4 | 152.9 | 147.1 |
| 33 | 168.6 | 178.1 | 168.1 | 187.3 | 173.35 | 177.7 |
| 34 | 133.4 | 124.3 | 122 | 125.5 | 128.85 | 123.75 |
| 35 | 162.9 | 164.1 | 159.9 | 170.8 | 163.5 | 165.35 |
| 36 | 154.5 | 154.5 | 161.1 | 144.4 | 154.5 | 152.75 |
| 37 | 165.9 | 168.5 | 162 | 163.1 | 167.2 | 162.55 |
| 38 | 168.8 | 167.1 | 177.9 | 178 | 167.95 | 177.95 |
| 39 | 149.6 | 151.3 | 142.5 | 143.8 | 150.45 | 143.15 |
| 40 | 130.4 | 128.7 | 134.5 | 133.6 | 129.55 | 134.05 |

TABLE 15

Statistics for an APOB multi-constituent mock calibrator using the Integra 400.

| | APOB | |
|---|---|---|
| Descriptive Statistics: | Test | Comparative |
| Mean | 102.5 | 89.5 |
| Median | 98.6 | 84.5 |
| Mode | 104.7 | 94.8 |
| SD | 28.1 | 28.4 |
| CV | 27.4 | 31.7 |
| Max | 186.3 | 170.2 |
| Min | 52.7 | 41.2 |
| Range | 133.6 | 129 |
| X − 2SD | 46.3 | 32.8 |
| X + 2SD | 158.7 | 146.2 |
| n | 80 | 80 |
| Duplicates | 40 | 40 |
| T = 0.980 * C + 14.810 | | |
| r = 0.988 | | |
| r2 = 0.977 | | |
| Sy/x = 4.344 | | |

(statistical terms defined elsewhere herein)

TABLE 16

Observed Data Based on Experimental Subjects, Using APOB Analyte and CFAS Lipid Calibration Reference

| | Test | | Comparative | | | |
|---|---|---|---|---|---|---|
| Sample # | Replicate 1 | Replicate 2 | Replicate 1 | Replicate 2 | Test Mean | Comparative Mean |
| 1 | 137.3 | 136.4 | 129 | 127.3 | 136.85 | 128.15 |
| 2 | 90.4 | 92.2 | 85.6 | 78.6 | 91.3 | 82.1 |
| 3 | 73.5 | 73.9 | 57.9 | 58.1 | 73.7 | 58 |
| 4 | 102.2 | 103.2 | 94.8 | 93 | 102.7 | 93.9 |
| 5 | 79 | 76.3 | 65.9 | 70.1 | 77.65 | 68 |
| 6 | 185.4 | 186.3 | 162 | 165.7 | 185.85 | 163.85 |
| 7 | 106.6 | 104.7 | 97.8 | 85.2 | 105.65 | 91.5 |
| 8 | 106.1 | 100.2 | 91 | 88.4 | 103.15 | 89.7 |
| 9 | 95.8 | 100.2 | 78.1 | 84.8 | 98 | 81.45 |
| 10 | 91.7 | 92 | 84.3 | 78.7 | 91.85 | 81.5 |
| 11 | 103.3 | 93.2 | 72.7 | 81.3 | 98.25 | 77 |
| 12 | 103.4 | 96.9 | 73.9 | 78.5 | 100.15 | 76.2 |
| 13 | 83.4 | 77.7 | 66.2 | 65.3 | 80.55 | 65.75 |
| 14 | 95.1 | 102 | 81.7 | 80.9 | 98.55 | 81.3 |
| 15 | 94.6 | 90.6 | 79.4 | 81.2 | 92.6 | 80.3 |
| 16 | 107.7 | 99.5 | 84.1 | 90 | 103.6 | 87.05 |
| 17 | 83.9 | 80.9 | 69.6 | 66.1 | 82.4 | 67.85 |
| 18 | 55.3 | 52.7 | 43.2 | 41.2 | 54 | 42.2 |
| 19 | 102 | 104.7 | 95.3 | 87.9 | 103.35 | 91.6 |
| 20 | 109.8 | 118.9 | 108.1 | 108.2 | 114.35 | 108.15 |
| 21 | 85.2 | 85.7 | 78.4 | 75.4 | 85.45 | 76.9 |
| 22 | 74.4 | 80.3 | 67 | 71.9 | 77.35 | 69.45 |
| 23 | 112.9 | 106.5 | 93.1 | 93.1 | 109.7 | 93.1 |
| 24 | 96.3 | 97.6 | 86.2 | 85.2 | 96.95 | 85.7 |
| 25 | 81.5 | 76.9 | 61.6 | 65.5 | 79.2 | 63.55 |
| 26 | 129.9 | 127.1 | 117.9 | 114.8 | 128.5 | 116.35 |
| 27 | 86.1 | 86.7 | 71.7 | 72.3 | 86.4 | 72 |
| 28 | 102.3 | 104.7 | 93.2 | 94.8 | 103.5 | 94 |
| 29 | 74.4 | 81 | 65.8 | 62.2 | 77.7 | 64 |
| 30 | 122.9 | 115.8 | 108.4 | 108.7 | 119.35 | 108.55 |
| 31 | 149.3 | 151.6 | 145.2 | 137.4 | 150.45 | 141.3 |
| 32 | 117 | 101.9 | 93.5 | 84.6 | 109.45 | 89.05 |
| 33 | 149.3 | 155.6 | 145.2 | 141.3 | 152.45 | 143.25 |
| 34 | 135.5 | 132.3 | 125.4 | 128.3 | 133.9 | 126.85 |
| 35 | 114.1 | 113.3 | 96.1 | 98.2 | 113.7 | 97.15 |
| 36 | 77 | 80.7 | 70.3 | 67.8 | 78.85 | 69.05 |
| 37 | 90.8 | 88 | 84.8 | 79.7 | 89.4 | 82.25 |
| 38 | 71.3 | 66.6 | 52 | 51.4 | 68.95 | 51.7 |
| 39 | 69.6 | 69.2 | 62.2 | 52 | 69.4 | 57.1 |
| 40 | 178.1 | 172.3 | 170.2 | 155.4 | 175.2 | 162.8 |

Example 5

Multi-Level Quality Control Set

Table 17 demonstrates a configuration that discloses three levels of a QC product used in routine QC testing in a clinical laboratory. Testing can occur on any or all levels, depending on the needs of the user.

TABLE 17

Multi-Level Quality Control Set

| QC Set | Units | Level 1 | Level 2 | Level 3 |
|---|---|---|---|---|
| Total Cholesterol | mg/dL | 100 | 250 | 500 |
| HDL | mg/dL | 20 | 50 | 100 |
| Triglycerides | mg/dL | 90 | 150 | 250 |
| LDL | mg/dL | 80 | 200 | 400 |
| APO A | mg/dL | 63 | 156 | 313 |
| APO B | mg/dL | 53 | 132 | 263 |

Similar to the Multi-Point Calibrator set disclosed previously elsewhere herein, the Quality Control set can be made as individual levels or from a dilution of the highest level.

Substantially pure lipid concentrates are assigned a value after being diluted to the appropriate instrument range and tested. Using the buffer prepared as set forth regarding the compositions disclosed in Table 1, the necessary amounts of components are added to make each level individually. The levels are then 0.2 µm filtered and tested.

The set points can be used without an assigned value. In such cases, the end user may establish their own values based on clinical specimens from their laboratory. However, these set points may also be run against a standard reference preparation and assigned a value. After an analyzer has been calibrated, the end user can run these levels to verify performance of the assay. Quality Control set points can also be used for troubleshooting. The compositions demonstrate extended stability compared with otherwise identical compositions that do not comprise TDPA.

Example 6

Multi-Level Quality Control

To illustrate that a lipid product as described above could be used for quality control, a Level 2 solution and a Level 3 solution from a formulation as described elsewhere herein were used as a control on the Integra 400 for 43 days. Data was collected and compared to the currently results obtained with Roche Preci controls for TRIG and CHOL, and Roche lipid controls for HDL, LDL, APOA and APOB. Those controls were run between 52-85 days, depending on the analyte. A comparison of the SD and CV for each analyte demonstrated that the material used was either equivalent to or better than the manufacturer's control material.

In addition to the Integra control study, a lipid product, with solutions of levels 2 and 5, were run in singlet over a period of 10 days on the Beckman Image for Lp(a). The Level 2 concentration was representative of the reference range, while the Level 3 concentration was outside of the range. The Level 2 data illustrated a range from 12.7-15.9 with a mean of 14.1 mg/dL. The Level 3 data illustrated a range from 49.5-59.8 with a mean of 54.2 mg/dL. The data is included in Table 19 below.

TABLE 18

Multi-Level Quality Control Using Roche Controls

|  | CHOL | HDL | LDL | APOA | APOB | TRIG |
|---|---|---|---|---|---|---|
| Level 2 QC |  |  |  |  |  |  |
| Mean | 107.61 | 42.44 | 101.26 | 162.17 | 80.54 | 106.12 |
| SD | 1.74 | 1.24 | 15.41 | 5.64 | 3.43 | 14.22 |
| CV | 1.62 | 2.93 | 15.22 | 3.48 | 4.26 | 13.4 |
| 2SD | 3.48 | 2.48 | 30.82 | 11.28 | 6.86 | 28.44 |
| X − 2SD | 104.13 | 39.96 | 70.44 | 150.89 | 73.68 | 77.68 |
| X + 2SD | 111.09 | 44.92 | 132.08 | 173.45 | 87.4 | 134.56 |
| Level 3 QC |  |  |  |  |  |  |
| Mean | 181.46 | 38.77 | 217.07 | 107.79 | 179.15 | 177.53 |
| SD | 3.07 | 39.11 | 6.93 | 4.24 | 7.2 | 3.67 |
| CV | 1.69 | 100.89 | 3.19 | 3.94 | 4.02 | 2.07 |
| 2SD | 6.14 | 78.22 | 13.86 | 8.48 | 14.4 | 7.34 |
| X − 2SD | 175.32 | −39.45 | 203.21 | 99.31 | 164.75 | 170.19 |
| X + 2SD | 187.6 | 116.99 | 230.93 | 116.27 | 193.55 | 184.87 |

(statistical terms defined elsewhere herein)

TABLE 19

Multi-Level Quality Control Material

|  | CHOL | HDL | LDL | APOA | APOB | TRIG | Lp(a) |
|---|---|---|---|---|---|---|---|
| Level 2 QC |  |  |  |  |  |  |  |
| Mean | 183.8 | 27.3 | 124 | 25.5 | 87.9 | 231.9 | 14.1 |
| SD | 3 | 0.7 | 2.3 | 3.1 | 6.4 | 3.6 | 1.0 |
| CV | 1.6 | 2.6 | 1.9 | 12 | 7.3 | 1.6 | 7.4 |
| 2SD | 6 | 1.4 | 4.6 | 6.1 | 12.8 | 7.2 | 2.0 |
| X − 2SD | 177.9 | 25.9 | 119.4 | 19.4 | 75.1 | 224.7 | 12.1 |
| X + 2SD | 189.8 | 28.7 | 128.6 | 31.6 | 100.7 | 239.1 | 16.1 |
| Level 3 QC |  |  |  |  |  |  |  |
| Mean | 368.9 | 51.5 | 249.9 | 69.5 | 178.5 | 455.4 | 54.2 |
| SD | 6.6 | 1.5 | 4.6 | 4 | 6.5 | 6.8 | 3.0 |
| CV | 1.8 | 2.9 | 1.9 | 5.7 | 3.6 | 1.5 | 5.5 |
| 2SD | 13.2 | 2.9 | 9.3 | 8 | 13 | 13.6 | 6.0 |
| X − 2SD | 355.8 | 48.6 | 240.7 | 61.5 | 165.5 | 441.8 | 48.2 |
| X + 2SD | 382.1 | 54.5 | 259.2 | 77.5 | 191.5 | 469.1 | 60.2 |

(statistical terms defined elsewhere herein)

Example 7

Calibration Verification and Linearity QC Set

Table 20 sets forth a configuration for a calibration verification and linearity test set using 5 equally spaced levels to cover the reportable range of a method being tested. Testing must use the low, mid and high points in order to cover the range needed to verify or confirm linearity.

TABLE 20

Calibration Verification and Linearity QC Set

| Calibrator | Units | Level 1 | Level 2 | Level 3 | Level 4 | Level 5 |
|---|---|---|---|---|---|---|
| Total Cholesterol | mg/dL | 100 | 275 | 450 | 625 | 800 |
| HDL | mg/dL | 25 | 48.75 | 72.5 | 96.25 | 120 |
| Triglycerides | mg/dL | 50 | 287.5 | 525 | 762.5 | 1000 |
| LDL | mg/dL | 75 | 226.25 | 377.5 | 528.75 | 680 |
| APO A | mg/dL | 78 | 152.25 | 226.5 | 300.75 | 375 |
| APO B | mg/dL | 49 | 150 | 251 | 352 | 453 |

Substantially pure lipid concentrates are assayed and assigned a value as set forth previously elsewhere herein. Using the buffer prepared as described previously for Table 1, Levels 1 and 5 are made by adding the appropriate amounts of lipid concentrates. Levels 1 and 5 are assayed. Adjustments are made so that each level is at the designated concentration. The levels are then re-tested and 0.2 µm filtered. The compositions demonstrate extended stability compared with otherwise identical compositions that do not comprise TDPA.

Levels 1 to 5 are prepared using the preferred "equal delta" method utilized by NCCLS's EP6 guideline for linearity testing. (NCCLS, 2003, In: Evaluation of the Linearity of Quantitative Measurement Procedures: A Statistical Approach, Approved Guideline, Vol. 23 (No. 16), Wayne, Pa.). Level 2 is prepared by combining 3 parts of level 1 with 1 part of level 5. Level 3 is made by adding equal parts of both levels 1 and 5. Level 4 is made by adding 1 part of level 1 and 3 parts of level 5. Each level is then tested to ensure the target concentration is reached. The calibration verification and linearity set may be run against a reference method for value assignment. Once established, the end user can run these 5 levels as patient samples and generate a linearity curve. The compositions demonstrate extended stability compared with otherwise identical compositions that do not comprise TDPA.

Example 8

Qualitative Cut-Offs

Table 21 sets forth a configuration for a point of care test (POCT) system wherein only qualitative results are reported. The materials are used to establish lower and upper cutoffs, or negative and positive results.

This material is produced as described previously elsewhere herein such as set forth with respect to a Two Point Calibrator Set. The negative reference can be a suitable blank material with "zero" amount of the desired component. The compositions demonstrate extended stability compared with otherwise identical compositions that do not comprise TDPA.

TABLE 21

Qualitative Cutoffs

| Qualitative Set | Units | Negative | Positive (Men) | Positive (Women) |
|---|---|---|---|---|
| Total Cholesterol | mg/dL | 0 | >240 | >240 |
| HDL | mg/dL | 0 | <35 | <45 |
| Triglycerides | mg/dL | 0 | 100 | 100 |
| LDL | mg/dL | 0 | >190 | >190 |
| APO-A | mg/dL | 0 | >120 | >120 |
| APO-B | mg/dL | 0 | <120 | <120 |

HDL-C plus Roche Product Insert 2002-02
LDL-C plus Roche Product Insert 2002-02
Cholesterol Gen.2 Roche Product Insert 2003-05
(2001, In: Appleton & Lange's Outline Review Clinical Chemistry, Christenson, Gregory and Johnson, eds., McGraw-Hill)

Example 9

Representative Composition

A sample composition, which demonstrates extended stability compared with otherwise identical compositions that do not comprise TDPA, is as follows:
  4.0 g/L TDPA
  0.9 g/L sodium azide
  40 ppm PROCLIN
  OXYRASE was added
in a buffer comprising HEPES, approximately pH 7.4 (pH ranging from about 7.2 to 7.6).

Stability of Composition:

Several formulations as disclosed previously elsewhere herein have been assayed to assess the stability of the composition using methods well-known in the art. Analyses to date demonstrate significantly less than 10% degradation over real time testing for a period of 6 months. Real time testing has been conducted at both refrigerated (e.g., 2-8° C.) and frozen temperatures (e.g., −10 to −20° C.) as storage conditions.

Stability testing continues and the compositions tested have demonstrated substantially less degradation compared with otherwise identical compositions to which TDPA was not added. Desired market stability is about from 12 to 15 months. The data disclosed herein demonstrate that the composition of the invention is stable to and through the desired market stability range. Testing has been conducted on formulations of between 4-9 grams per liter TDPA with and without OXYRASE present and the stability of the various formulations is approximated equal.

Example 10

Use of Various Antioxidants in Standard Solutions

Antioxidants chosen and tested included Phytic Acid Dodecasodium Salt, N-acetyl-L-cysteine, BHT, Ascorbic Acid, Fumaric Acid, EDTA, Monothioglycerol, Propyl Gallate, Hydroquinone, Isoascorbic Acid, Phytic Acid Dipotassium Salt and Cysteamine HCL.

TABLE 22

Primary Antioxidants

| | Phenols | "Hindered Phenols" | Miscellaneous Primary Antioxidants |
|---|---|---|---|
| PRIMARY ANTIOXIDANTS (Terminate the free radical chain reaction by acting as hydrogen or electron donors to free radicals, resulting in the formation of more stable products) | Dodecyl Gallate Octyl Gallate Propyl Gallate Hydroquinone Trihydroxy-butyrophenone Nordihydro-guaiaretic Acid | BHA BHT TBHQ Tocopherol Tocophersolan Tocopheryl Acetate Tocopheryl Linoleate Tocopheryl Nicotinate Tocopheryl Succinate Gum Guaric Ionox Series Vitamin E | Ethoxyquin Anoxomer Trolox-C |

TABLE 23

Secondary or Synergistic Antioxidants

| | Oxygen scavengers | Chelating agents | Secondary antioxidants | Miscellaneous Secondary Antioxidants |
|---|---|---|---|---|
| SECONDARY/ SYNERGISTIC ANTIOXIDANTS (broadly classified as oxygen scavengers and | Disodium Ascorbyl Sulfate Hydrazine Sulfate Sodium Bisulfate Sodium Metabisulfate | Polyphosphates Phosphoric acid EDTA Tartaric Acid | 3,3 TDPA Dilaurel, Distearyl Esters Dilaurel Thiodipropionate, Dimyristyl | Sodium Nitrate Sodium Nitrite Amino Acids Cysteine Cysteine HCL Cysteamine HCL |

TABLE 23-continued

Secondary or Synergistic Antioxidants

| Oxygen scavengers | Chelating agents | Secondary antioxidants | Miscellaneous Secondary Antioxidants |
|---|---|---|---|
| chelators) | Ascorbic Acid | Citric Acid | Thiodipropionate, | Acetyl Cysteine |
| | Isoascorbic Acid | Citrate | Dicetyl | Histidine |
| | Allantoin | Esters | Thiodipropionate, | Hydrochloride |
| | Ascorbate | Acetyl | Distearyl | |
| | Magnesium | Trihexyl | Thiodipropionate, | |
| | Ascorbate | Citrate | Ditridecyl | |
| | Methylsilanol | Triethyl | Thiodipropionate | |
| | Ascorbate | Citrate | | |
| | Ascorbyl | Phytic Acid | | |
| | Palmitate | Lecithin | | |
| | Ascorbyl | | | |
| | Methylsilanol | | | |
| | Palmitate | | | |
| | Ascorbyl | | | |
| | Dipalmitate | | | |
| | Ascorbyl Stearate | | | |
| | Erythorbic Acid | | | |
| | Sodium | | | |
| | Erythorbate | | | |

TABLE 24

Miscellaneous Antioxidants

| | |
|---|---|
| 4,4 Isopropylidenediphenol | Dihydroxymaleic Acid |
| Decyl Mercaptomethylimidazole | N,N'-Diphenol-p-phenylenediamine |
| Diamylhydroquinone | Edetic Acid |
| Digalloyl Trileate | Ethanethiol |
| Dioleyl Tocopheryl Methylsilanol | Fumaric Acid |
| Hydroxylamine HCL | Gallic Acid |
| Hydroxylamine Sulfate | Gossypol |
| Lysine Hydrochloride | Hydrazine |
| o-Tolyl Biguanide | 4'-Hydroxybutyranilide |
| Phenylthioglycolic Acid | Hydroxylamine |
| Sorbityl Furfural | Isobutylene |
| Thiodiglycol | Morpholine |
| Thiodiglycolamide | 1,8-Naphthalenediamine |
| Thiolactic Acid | 2-Napthol |
| Thiosalicylic Acid | 2-Napthylamine |
| Tris(Nonphenyl)Phosphite | N-Nitrosodiethylamine |
| Acrylonitrile | N-Nitrosodiemethylamine |
| p-Biphenylamine | Reductic Acid |
| p-tert-Butylphenol | Sucrose |
| Chloroacetone | Thionine |
| Crotonaldehyde | Thymol |
| Cupric Oleate | Tocol |
| DBHBT | Xibornal |
| Dibenzyl Disulfide | Monothioglycerol |

Solutions were prepared using a formulation for a lipid product as described elsewhere herein, using 22 mM TDPA, OXYRASE and HEPES buffer. Anti-oxidants were classified (Tables 22-24) and one from each grouping was selected. Subsequent Level 5 solutions were prepared using the selected anti-oxidants (no TDPA) at the same concentration as TDPA. Solutions were aliquoted and stored at room temperature, at 2-8° C. and at −10 to −20° C. Periodically, the stored aliquots were tested for HDL, LDL, TRIG, CHOL, APOA and APOB. The goal of this testing was to determine the protective effect that the various anti-oxidants had on the lipid product at the different temperatures.

TABLE 25

Percent recovery of HDL as a function of antioxidant at multiple storage temperatures. Percent recovery refers to the concentration relative to the initial concentration for each configuration.

| HDL | room temperature | 4° C. | −20° C. | Hours |
|---|---|---|---|---|
| 18 g/L TDPA | 30.30% | 60.00% | 231.10% | 552 |
| Monothioglycerol | 103.20% | 109% | 109.80% | 504 |
| Fumaric Acid | 28.90% | 96.90% | 103.50% | 528 |
| EDTA | 78.20% | 98.70% | 99.80% | 528 |
| BHT | 85.00% | 95.40% | 98.60% | 528 |
| N-acetyl-L-cysteine | 90.10% | 100.90% | 98.00% | 552 |
| Oxyrase ™ | 75.20% | 93.40% | 98% | 552 |
| Ascorbic Acid | 21.40% | 67.40% | 95.90% | 528 |
| Phytic Acid Dodecasodium Salt | 115.40% | 100.20% | 93.90% | 552 |
| Oxyrase ™ + 4 g/L TDPA | 32.20% | 89.10% | 93.30% | 552 |

TABLE 26

Percent recovery of LDL as a function of antioxidant at multiple storage temperatures

| LDL | room temperature | 4° C. | −20° C. | Hours |
|---|---|---|---|---|
| Fumaric Acid | 98.50% | 100.10% | 100.20% | 528 |
| Phytic Acid Dodecasodium Salt | 100.90% | 99.50% | 99.50% | 552 |
| N-acetyl-L-cysteine | 101.70% | 99.30% | 99.50% | 552 |
| EDTA | 100.00% | 97.10% | 99.20% | 528 |
| Monothioglycerol | 101.20% | 97% | 96.20% | 504 |
| BHT | 101.60% | 94.90% | 96.00% | 528 |
| Oxyrase ™ | 95.00% | 95.70% | 96% | 552 |
| Oxyrase ™ + 4 g/L TDPA | 95.70% | 93.40% | 93.90% | 552 |
| Ascorbic Acid | 44.60% | 69.60% | 87.80% | 528 |
| 18 g/L TDPA | 82.00% | 99.80% | 49.50% | 552 |

TABLE 27

Percent recovery of APOA as a function of antioxidant at multiple storage temperatures

| APOA | room temperature | 4° C. | −20° C. | Hours |
|---|---|---|---|---|
| Fumaric Acid | 24.70% | 121.30% | 134.00% | 528 |
| BHT | 70.30% | 100.00% | 113.90% | 528 |
| Monothioglycerol | 67.30% | 100% | 111.40% | 504 |
| Ascorbic Acid | 54.40% | 85.80% | 109.80% | 528 |
| Oxyrase ™ + 4 g/L TDPA | 27.70% | 108.30% | 106.70% | 552 |
| Phytic Acid Dodecasodium Salt | 64.90% | 86.00% | 102.90% | 552 |
| N-acetyl-L-cysteine | 70.30% | 89.80% | 97.50% | 552 |
| Oxyrase ™ | 44.60% | 82.50% | 97% | 552 |
| EDTA | 34.10% | 78.90% | 91.90% | 528 |
| 18 g/L TDPA | 50.80% | 90.60% | 67.60% | 552 |

TABLE 28

Percent recovery of APOB as a function of antioxidant at multiple storage temperatures

| APOB | room temperature | 4° C. | −20° C. | Hours |
|---|---|---|---|---|
| Oxyrase ™ + 4 g/L TDPA | 102.40% | 115.00% | 116.90% | 552 |
| Oxyrase ™ | 78.80% | 103.20% | 113% | 552 |
| N-acetyl-L-cysteine | 94.50% | 95.70% | 104.30% | 552 |
| Phytic Acid Dodecasodium Salt | 82.10% | 85.60% | 95.10% | 552 |
| 18 g/L TDPA | 44.30% | 102.80% | 94.50% | 552 |
| Fumaric Acid | 76.70% | 83.60% | 87.30% | 528 |
| EDTA | 56.80% | 69.00% | 83.10% | 528 |
| BHT | 63.10% | 71.60% | 80.30% | 528 |
| Ascorbic Acid | 58.50% | 72.20% | 80.30% | 528 |
| Monothioglycerol | 65.60% | 70% | 75.90% | 504 |

TABLE 29

Percent recovery of CHOL as a function of antioxidant at multiple storage temperatures

| CHOL | room temperature | 4° C. | −20° C. | Hours |
|---|---|---|---|---|
| Ascorbic Acid | 1078.30% | 634.30% | 215.50% | 528 |
| Monothioglycerol | 205.50% | 202% | 148.80% | 504 |
| N-acetyl-L-cysteine | 208.10% | 207.70% | 116.70% | 552 |
| Fumaric Acid | 99.80% | 101.20% | 102.60% | 528 |
| BHT | 103.90% | 103.90% | 102.00% | 528 |
| EDTA | 100.30% | 103.00% | 99.10% | 528 |
| Oxyrase ™ | 97.50% | 97.00% | 99% | 552 |
| Phytic Acid Dodecasodium Salt | 97.50% | 94.80% | 97.40% | 552 |
| Oxyrase ™ + 4 g/L TDPA | 94.40% | 95.00% | 95.10% | 552 |
| 18 g/L TDPA | 92.10% | 98.00% | 82.60% | 552 |

TABLE 30

Percent recovery of TRIG as a function of antioxidant at multiple storage temperatures

| TRIG | room temperature | 4° C. | −20° C. | Hours |
|---|---|---|---|---|
| Monothioglycerol | 400.40% | 382% | 196.80% | 504 |
| Ascorbic Acid | 531.30% | 212.50% | 131.30% | 528 |
| N-acetyl-L-cysteine | 348.60% | 330.50% | 125.70% | 552 |
| Fumaric Acid | 102.10% | 103.50% | 104.30% | 528 |
| EDTA | 102.50% | 104.20% | 102.40% | 528 |
| Phytic Acid Dodecasodium Salt | 105.80% | 99.90% | 101.10% | 552 |
| Oxyrase ™ | 105.90% | 100.90% | 101% | 552 |
| BHT | 110.50% | 103.20% | 101.10% | 528 |
| Oxyrase ™ + 4 g/L TDPA | 100.00% | 99.90% | 100.60% | 552 |
| 18 g/L TDPA | 84.90% | 99.60% | 79.80% | 552 |

Example 11

Characterization of the Degradation of Lipid Materials in a Combination Antioxidant Buffer HDL and LDL concentrates were prepared in a buffer that included N-acetyl-cysteine and Fumaric Acid. Level 5 solutions were prepared as previously described. The samples were frozen, thawed and stored at the following temperatures/ranges: 20° C. (RT), 2-8° C. and −20° C. Testing was conducted every 48 hours for four weeks.

Previous studies showed that N-acetyl-L-cysteine only recovered in the same manner as the N-acetyl-L-cysteine and Fumaric Acid combination. Fumaric Acid only recovered better in CHOL and TRIG in previous studies, while APO-A improved in the present formulation. The combination of N-acetyl-L-cysteine and Fumaric Acid at −20° C. recovers well in most tests.

TABLE 31

Percent Recovery of specific analytes with a combination of antioxidants.

| | Percent Recovery @ −20 C. after 744 hours | | | | | |
|---|---|---|---|---|---|---|
| | HDL | LDL | APO-A | APO-B | TCHOL | TRIG |
| N-acetyl-L-cysteine and Fumaric Acid | 96 | 102.3 | 96.8 | 105.6 | 131.3 | 148.7 |
| N-acetyl-L-cysteine | 101 | 99 | 99.8 | 103.2 | 134.7 | 150.5 |
| Fumaric Acid | 97.9 | 99.6 | 107.1 | 105.2 | 102.3 | 102.4 |

Example 12

Effect of Buffer Composition on Stabilization of Standard Solution

Solutions were prepared using a formulation for a lipid product as described elsewhere herein, using 4 g/L TDPA, OXYRASE and HEPES. Subsequent Level 5 solutions were prepared (using no HEPES) using various buffers (BES, MOPS and TRIS) at the same concentration as HEPES. Solutions were aliquoted and stored at room temperature, 2-8° C. and −10 to −20° C. Periodically, the aliquots were tested for HDL, LDL, TRIG, CHOL, APOA and APOB. The goal of this testing was to determine the protective effect that the various buffers had on the lipid product at the different temperatures.

The data after 528 hours showed that HEPES buffer provided the most protective effect. All other buffers tested did provide protection, but not at the same level as HEPES buffer.

TABLE 32

Percent recovery of standards as a function of buffer and temperature. Data are provided as a percentage of initial concentration.

| Buffer | room temp | 4° C. | −20° C. | Hours |
|---|---|---|---|---|
| HDL Recovery | | | | |
| MOPS Buffer | 47.50% | 91.90% | 98.40% | 528 |
| Tris Buffer | 77.30% | 97.70% | 97.60% | 528 |
| BES Buffer | 77.30% | 93% | 95.90% | 528 |
| HEPES Buffer | 32.20% | 89.10% | 93.30% | 552 |
| LDL Recovery | | | | |
| BES Buffer | 100.60% | 97% | 378.20% | 528 |
| MOPS Buffer | 102.50% | 95.20% | 376.70% | 528 |
| Tris Buffer | 97.00% | 95.40% | 99.10% | 528 |
| HEPES Buffer | 95.70% | 93.40% | 93.90% | 552 |
| APOA Recovery | | | | |
| HEPES Buffer | 27.70% | 108.30% | 106.70% | 552 |
| MOPS Buffer | 33.80% | 78.30% | 91.70% | 528 |
| BES Buffer | 40.20% | 78% | 90.70% | 528 |
| Tris Buffer | 33.80% | 72.50% | 86.10% | 528 |
| APOB Recovery | | | | |
| HEPES Buffer | 102.40% | 115.00% | 116.90% | 552 |
| MOPS Buffer | 57.80% | 82.80% | 89.70% | 528 |
| Tris Buffer | 49.30% | 71.70% | 80.80% | 528 |
| BES Buffer | 54.50% | 71% | 80.40% | 528 |
| CHOL Recovery | | | | |
| BES Buffer | 101.20% | 97% | 100.90% | 528 |
| Tris Buffer | 101.10% | 98.50% | 100.90% | 528 |
| MOPS Buffer | 100.20% | 96.80% | 97.30% | 528 |
| HEPES Buffer | 94.40% | 95.00% | 95.10% | 552 |
| TRIG Recovery | | | | |
| HEPES Buffer | 100.00% | 99.90% | 100.60% | 552 |
| Tris Buffer | 111.30% | 102.70% | 100.40% | 528 |
| BES Buffer | 109.90% | 103% | 99.10% | 528 |
| MOPS Buffer | 99.00% | 97.80% | 97.20% | 528 |

An additional study was conducted in order to characterize the degradation of the lipid raw materials (HDL and LDL concentrates) in a Sodium Phosphate buffer that included OXYRASE and 4 g/L TDPA. Lipid buffer with the addition of Sodium Phosphate was prepared and a level 5 was generated, as described elsewhere herein. The samples were frozen, thawed and stored at the following temperatures/ranges: 20° C. (RT), 2-8° C. and −20° C. Testing was conducted every 48 hours for four weeks.

After 672 hours of testing the following results were observed. APO-A and APO-B in Level 5 solutions with Sodium Phosphate buffer degraded over time compared to the Level 5 solutions containing HEPES, demonstrated in data set forth elsewhere herein, which increased. APO-A in Sodium Phosphate buffer at −20° C. recovered at 95% after 624 hours while APO-A in HEPES buffer recovered at 113% after 600 hours. APO-B in Sodium Phosphate buffer at −20° C. recovered at 97% after 624 hours while APO-B in HEPES buffer recovered at 113% after 600 hours. Level 5 solutions with Sodium Phosphate buffer recovered well in all tests at −20° C. (~98%), followed by 2-8° C. (~93%).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A stable aqueous lipid reference standard composition comprising a substantially pure constituent of known value, wherein said constituent is selected from at least one of the group consisting of total cholesterol (CHOL), triglycerides (TRIG) originating from a biological sample, low density lipoprotein (LDL), high density lipoprotein (HDL), apolipoprotein A (APO-A), apolipoprotein B (APO-B), apolipoprotein a (Lp(a)), and a subcomponent of an apolipoprotein, said reference standard composition further comprising a stabilizing amount of 3,3'-thiodipropionic acid (TDPA), said reference standard composition ranging in pH from about 6.5 to 9.0.

2. The reference composition of claim 1, wherein said reference composition is useful for at least one use selected from the group consisting of calibration, quality control, calibration verification, and assessment of linearity, and further wherein said composition is useful in a pH range from about 6.5 to 8.3.

3. The reference composition of claim 2, wherein said use comprises a manual, semi-automated, and fully-automated method comprising an instrument for measurement of said constituent.

4. The reference composition of claim 1, wherein said stabilizing amount ranges from about 1.1 grams per liter to 18.0 grams per liter.

5. The reference composition of claim 1, wherein said subcomponent is at least one subcomponent selected from the group consisting of AII, AIV, B-48, B-100, CI, CII, CIII, D, E1, E2, E3, E4, E5, E6, F, G, H, and J.

6. The reference composition of claim 1, wherein said value of CHOL ranges from about 0 to 5000 mg/dL.

7. The reference composition of claim 1, wherein said value of triglycerides ranges from about 0 to 4000 mg/dL.

8. The reference composition of claim 1, wherein said value of LDL ranges from about 0 to 5000 mg/dL.

9. The reference composition of claim 1, wherein said value of HDL ranges from about 0 to 1000 mg/dL.

10. The reference composition of claim 1, wherein said value of APO-A ranges from about 0 to 1000 mg/dL.

11. The reference composition of claim 1, wherein said value of APO-B ranges from about 0 to 1000 mg/dL.

12. The reference composition of claim 1, wherein said value of Lp(a) ranges from about 0 to 1200 mg/dL.

13. The reference composition of claim 1, wherein said value of said subcomponent ranges from about 0 to 500 mg/dL.

14. The reference composition of claim 1, said composition further comprising a buffer comprising N-2-hydroxyethylpiperazine-N-2-ethane sulphonic acid (HEPES) such that said composition ranges in pH from about 6.5 to 8.3.

15. The reference composition of claim 1, said composition further comprising a buffer selected from the group consisting of: a buffer comprising N,N-Bis(2-hydroxyethyl)-2-aminoethanesulfonic acid (BES) such that said composition ranges in pH from about 6.8 to 8.3; a buffer comprising 3-(N-Morpholino)propanesulfonic acid (MOPS) such that said composition ranges in pH from about 6.8 to 8.3; a buffer comprising N-[Tris(hydroxymethyl)methyl]-2-aminoethanesulfonic acid (TES) such that said composition ranges in pH from about 6.8 to 8.3; a buffer comprising Tris(hydroxylmethyl)aminomethane (TRIS) such that said composition ranges in pH from about 6.8 to 8.3; and a buffer comprising Sorenson's Phosphate buffer such that said composition ranges in pH from about 6.8 to 8.3.

16. The reference composition of claim 1, said composition further comprising an amount of sodium azide less than about 0.09% (weight/volume).

17. The reference composition of claim 1, said composition further comprising generic terminology-2-methyl-4-isothiazlin-3-one in an amount ranging from about 10 parts per million (ppm) to 100 ppm.

18. The reference composition of claim 1, said composition further comprising cell membrane fragments obtained from E. coli in an amount ranging from about 0.05 U/mL to 0.5 U/mL.

19. A method for producing the reference composition of claim 1, said method comprising mixing a liquid comprising water, with a known value of a substantially pure constituent to produce a mixture and further adding a stabilizing amount of 3,3'-thiodipropionic acid to said mixture.

20. A method for calibration, quality control, calibration verification, or assessment of linearity of an instrument wherein said instrument is used to measure an amount of a constituent in a test solution, said method comprising subjecting said instrument to calibration, quality control, calibration verification, or assessment of linearity with the reference composition of claim 1.

21. The method of claim 20, wherein said use provides information related to the condition of a living subject, said condition being selected from the group consisting of a cholesterol level, a triglyceride level, an HDL level, an LDL level, an Apo-A level, an Apo-B level, and an Lp(a) level, in support of the diagnosis, treatment, and/or monitoring of, but not limited to, coronary artery disease, atherosclerosis, diabetes mellitus, various hyperlipidemias, genetic abnormalities of lipoprotein metabolism, obstructive liver disease, renal insufficiency, and hypothyroidism.

22. A method for calibration, quality control, calibration verification, or assessment of linearity of an instrument used to measure the amount of an analyte in a test solution, said method comprising subjecting said instrument to calibration, quality control, calibration verification, or assessment of linearity with the composition of claim 1.

23. The method of claim 22, wherein said use provides information related to the condition of a living subject, said condition being selected from the group consisting of a cholesterol level, a triglyceride level, an HDL level, an LDL level, an Apo-A level, an Apo-B level, and an Lp(a) level, in support of the diagnosis, treatment, and/or monitoring of, but not limited to, coronary artery disease, atherosclerosis, diabetes mellitus, various hyperlipidemias, genetic abnormalities of lipoprotein metabolism, obstructive liver disease, renal insufficiency, hypothyroidism.

24. A stable control or calibration standard composition comprising a stabilizing amount of 3,3'-thiodipropionic acid, said composition further comprising a predetermined content of substantially pure analyte, wherein said analyte is at least one analyte selected from the group consisting of total cholesterol (CHOL), triglycerides (TRIG) originating from a biological sample, low density lipoprotein (LDL), high density lipoprotein (HDL), apolipoprotein A (APO-A), apolipoprotein B (APO-B), Lp(a) and a subcomponent of an apolipoprotein.

25. A method for producing a stable control composition, said method comprising mixing an aqueous solution with a stabilizing amount of 3,3'-thiodipropionic acid, and further comprising adding a predetermined amount of an essentially pure analyte, wherein said analyte is at least one analyte selected from the group consisting of total cholesterol (CHOL), triglycerides (TRIG) originating from a biological sample, low density lipoprotein (LDL), high density lipoprotein (HDL), apolipoprotein A (APO-A), apolipoprotein B (APO-B), Lp(a) and a subcomponent of an apolipoprotein.

26. The method of claim 25, wherein said aqueous solution is selected from the group consisting of water, plasma, serum, a solution comprising bovine serum albumin, a solution comprising human serum albumin, a solution comprising gamma globulin, and a solution comprising a Good's Buffer.

27. The method of claim 25, said method further comprising adding to said mixture an effective amount of an antimicrobial.

28. A kit for calibration, quality control, calibration verification, or assessment of linearity of an instrument used to measure the amount of a constituent in a test solution, said kit comprising a composition comprising a known amount of said constituent and a stabilizing amount of 3,3'-thiodipropionic acid (TDPA), said kit further comprising an applicator and an instructional material for the use of said kit, wherein said constituent is substantially pure, further wherein said constituent is selected from at least one of the group consisting of total cholesterol (CHOL), triglycerides (TRIG) originating from a biological sample, low density lipoprotein (LDL), high density lipoprotein (HDL), apolipoprotein A (APO-A), apolipoprotein B (APO-B), apolipoprotein a (Lp(a)), and a subcomponent of an apolipoprotein.

29. The kit of claim 28, wherein said composition comprises about 4.0 g/L TDPA, about 0.9 g/L sodium azide, about 40 ppm 2-methyl-4-isothiazlin-3-one, and further comprises HEPES buffer at about pH 7.4, wherein the pH of said composition ranges from about pH 7.2 to 7.6.

30. The kit of claim 28, wherein said kit comprises at least one composition selected from the group consisting of: a) a composition comprising about 10 mg/dL total cholesterol, about 5 mg/dL HDL, about 0 mg/dL triglycerides, about 5 mg/dL LDL, about 15.6 mg/dL APO-A, and about 3.3 mg/dL APO-B; b) a composition comprising about 200 mg/dL total cholesterol, about 37.5 mg/dL HDL, about 250 mg/dL triglycerides, about 162.5 mg/dL LDL, about 117.2 mg/dL APO-A, and about 106.9 mg/dL APO-B; c) a composition comprising about 400 mg/dL total cholesterol, about 115 mg/dL HDL, about 500 mg/dL triglycerides, about 285 mg/dL LDL, about 359.4 mg/dL APO-A, and about 187.5 mg/dL APO-B; d) a composition comprising about 600 mg/dL total cholesterol, about 177.5 mg/dL HDL, about 750 mg/dL triglycerides, about 422.5 mg/dL LDL, about 554.7 mg/dL APO-A, and about 287.0 mg/dL APO-B; and e) a composition comprising about 800 mg/dL total cholesterol, about 200 mg/dL HDL, about 1000 mg/dL triglycerides, about 600 mg/dL LDL, about 625 mg/dL APO-A, and about 394.7 mg/dL APO-B.

31. The kit of claim 28, wherein said kit comprises at least one composition selected from the group consisting of: a) a composition comprising about 0 mg/dL total cholesterol, about 0 mg/dL HDL, about 0 mg/dL triglycerides, about 0 mg/dL LDL, about 0 mg/dL APO-A, and about 0 mg/dL APO-B; and b) a composition comprising about 200 mg/dL total cholesterol, about 60 mg/dL HDL, about 250 mg/dL triglycerides, about 140 mg/dL LDL, about 188 mg/dL APO-A, and about 92 mg/dL APO-B.

32. The kit of claim 28, wherein said kit comprises at least one composition selected from the group consisting of: a) a composition comprising about 100 mg/dL total cholesterol, about 20 mg/dL HDL, about 90 mg/dL triglycerides, about 80 mg/dL LDL, about 63 mg/dL APO-A, and about 53 mg/dL APO-B; b) a composition comprising about 250 mg/dL total cholesterol, about 50 mg/dL HDL, about 150 mg/dL triglycerides, about 200 mg/dL LDL, about 156 mg/dL APO-A, and about 132 mg/dL APO-B; and c) a composition comprising about 500 mg/dL total cholesterol, about 100 mg/dL HDL, about 250 mg/dL triglycerides, about 400 mg/dL LDL, about 313 mg/dL APO-A, and about 263 mg/dL APO-B.

33. The kit of claim 28, wherein said kit comprises at least one composition selected from the group consisting of: a) a composition comprising about 100 mg/dL total cholesterol, about 25 mg/dL HDL, about 50 mg/dL triglycerides, about 75 mg/dL LDL, about 78 mg/dL APO-A, and about 49 mg/dL APO-B; b) a composition comprising about 275 mg/dL total cholesterol, about 48.75 mg/dL HDL, about 287.5 mg/dL triglycerides, about 226.25 mg/dL LDL, about 152.25 mg/dL APO-A, and about 150 mg/dL APO-B; c) a composition comprising about 450 mg/dL total cholesterol, about 72.5 mg/dL HDL, about 525 mg/dL triglycerides, about 377.5 mg/dL LDL, about 226.5 mg/dL APO-A, and about 251 mg/dL APO-B; d) a composition comprising about 625 mg/dL total cholesterol, about 96.25 mg/dL HDL, about 762.5 mg/dL triglycerides, about 528.75 mg/dL LDL, about 300.75 mg/dL APO-A, and about 352 mg/dL APO-B; and e) a composition comprising about 800 mg/dL total cholesterol, about 120 mg/dL HDL, about 1000 mg/dL triglycerides, about 680 mg/dL LDL, about 375 mg/dL APO-A, and about 453 mg/dL APO-B.

34. The kit of claim 28, wherein said kit comprises at least one composition selected from the group consisting of: a) a composition comprising about 0 mg/dL total cholesterol, about 0 mg/dL HDL, about 0 mg/dL triglycerides, about 0 mg/dL LDL, about 0 mg/dL APO-A, and about 0 mg/dL APO-B; and b) a composition comprising greater than about 240 mg/dL total cholesterol, less than about 35 mg/dL HDL, about 100 mg/dL triglycerides, greater than about 190 mg/dL LDL, greater than about 120 mg/dL APO-A, and less than about 120 mg/dL APO-B.

35. The kit of claim 28, wherein said kit comprises at least one composition selected from the group consisting of: a) a composition comprising about 0 mg/dL total cholesterol, about 0 mg/dL HDL, about 100 mg/dL triglycerides, about 0 mg/dL LDL, about 0 mg/dL APO-A, and about 0 mg/dL APO-B; and b) a composition comprising greater than about 240 mg/dL total cholesterol, less than about 45 mg/dL HDL, about 100 mg/dL triglycerides, greater than about 190 mg/dL LDL, greater than about 120 mg/dL APO-A, and less than about 120 mg/dL APO-B.

36. A method for producing a calibration standard composition, said method comprising mixing an aqueous solution with a stabilizing amount of 3,3'-thiodipropionic acid, and further comprising adding a predetermined amount of an essentially pure analyte, wherein said analyte is at least one analyte selected from the group consisting of total cholesterol (CHOL), triglycerides (TRIG) originating from a biological sample, low density lipoprotein (LDL), high density lipoprotein (HDL), apolipoprotein A (APO-A), apolipoprotein B (APO-B), Lp(a) and a subcomponent of an apolipoprotein.

37. A method for producing a linearity test set composition, said method comprising mixing an aqueous solution with a stabilizing amount of 3,3'-thiodipropionic acid, and further comprising adding a predetermined amount of an essentially pure analyte, wherein said analyte is at least one analyte selected from the group consisting of total cholesterol (CHOL), triglycerides (TRIG) originating from a biological sample, low density lipoprotein (LDL), high density lipoprotein (HDL), apolipoprotein A (APO-A), apolipoprotein B (APO-B), Lp(a) and a subcomponent of an apolipoprotein.

38. A method for producing a calibration verification test set composition, said method comprising mixing an aqueous solution with a stabilizing amount of 3,3'-thiodipropionic acid, and further comprising adding a predetermined amount of an essentially pure analyte, wherein said analyte is at least one analyte selected from the group consisting of total cholesterol (CHOL), triglycerides (TRIG) originating from a biological sample, low density lipoprotein (LDL), high density lipoprotein (HDL), apolipoprotein A (APO-A), apolipoprotein B (APO-B), Lp(a) and a subcomponent of an apolipoprotein.

* * * * *